(12) United States Patent
Hiernaux et al.

(10) Patent No.: US 9,986,996 B2
(45) Date of Patent: Jun. 5, 2018

(54) DEVICE FOR SUPPORTING AN ENDOSCOPIC TOOL

(71) Applicant: ENDO TOOLS THERAPEUTICS S.A., Gosselies (BE)

(72) Inventors: Martin Hiernaux, Watermael-Boitsfort (BE); Alexandre Chau, Koekelberg (BE); Jacques Deviere, Braine-le-Comte (BE); Vincent Huberty, Uccle (BE); Mostapha Ibrahim, Gizah (EG)

(73) Assignee: ENDO TOOLS THERAPEUTICS S.A., Gosselies (BE)

( * ) Notice: Subject to any disclaimer, the term of this patent is extended or adjusted under 35 U.S.C. 154(b) by 142 days.

(21) Appl. No.: 15/025,412

(22) PCT Filed: Oct. 10, 2014

(86) PCT No.: PCT/EP2014/071781
§ 371 (c)(1),
(2) Date: Mar. 28, 2016

(87) PCT Pub. No.: WO2015/052320
PCT Pub. Date: Apr. 16, 2015

(65) Prior Publication Data
US 2016/0235400 A1    Aug. 18, 2016

(30) Foreign Application Priority Data

Oct. 11, 2013   (EP) ..................................... 13188236

(51) Int. Cl.
*A61B 17/04* (2006.01)
*A61B 17/00* (2006.01)
(Continued)

(52) U.S. Cl.
CPC ........ *A61B 17/0469* (2013.01); *A61B 1/0014* (2013.01); *A61B 17/062* (2013.01);
(Continued)

(58) Field of Classification Search
CPC .............. A61B 17/0469; A61B 17/062; A61B 17/0482; A61B 2017/00296;
(Continued)

(56) References Cited

U.S. PATENT DOCUMENTS

2004/0138682 A1   7/2004   Onuki et al.
2005/0234294 A1   10/2005  Saadat et al.
(Continued)

FOREIGN PATENT DOCUMENTS

WO   2005122862 A2   12/2005
WO   2007104397 A1   9/2007

OTHER PUBLICATIONS

International Search Report from the European Patent Office in International Application No. PCT/EP2014/071781 dated Jan. 29, 2015.

*Primary Examiner* — Timothy J Neal
(74) *Attorney, Agent, or Firm* — The Marbury Law Group, PLLC

(57) ABSTRACT

A device for supporting an endoscopic tool is disclosed comprising attachment means for attaching the device to an endoscope, a first guide tube having a distal open end and configured for accepting the endoscopic tool through it, first and second projecting members extending distally of the attachment means and being spaced apart when the device is attached to the endoscope to define a working space between them. The attachment means comprise first and second clamping members and at least one cable linking the clamping members. The cable is remotely actuatable for moving the clamping members relative to each other to adjust a (Continued)

spacing between them, accepting an endoscope. The cable allows for securing the clamping members to the endoscope. The first projecting member is attached to the first clamping member such that it has a fixed or at least one fixable position relative to the first clamping member, and the second projecting member is attached to the second clamping member. The first guide tube is slidable relative to the first clamping member, and the distal end of the first guide tube is pivotally attached to a distal end of the first projecting member so as to enable the distal end of the first guide tube to be pivoted to an orientation transverse to the first projecting member.

20 Claims, 17 Drawing Sheets

(51) Int. Cl.
    *G02B 23/24*     (2006.01)
    *A61B 17/062*     (2006.01)
    *A61B 1/00*     (2006.01)
    *A61B 1/018*     (2006.01)

(52) U.S. Cl.
    CPC ...... *G02B 23/2476* (2013.01); *A61B 1/00087* (2013.01); *A61B 1/00098* (2013.01); *A61B 1/018* (2013.01); *A61B 17/0482* (2013.01); *A61B 2017/00296* (2013.01); *A61B 2017/00477* (2013.01); *A61B 2017/00818* (2013.01)

(58) Field of Classification Search
    CPC ........ A61B 2017/00818; A61B 1/0014; A61B 1/00087; A61B 1/00098; A61B 1/018; A61B 1/00112; A61B 1/00128; G02B 23/2476
    See application file for complete search history.

(56) References Cited

U.S. PATENT DOCUMENTS

2005/0234297 A1    10/2005    Devierre et al.
2005/0251166 A1    11/2005    Vaughan et al.
2007/0197862 A1    8/2007    Deviere et al.

DEVICE FOR SUPPORTING AN ENDOSCOPIC TOOL

RELATED APPLICATIONS

This application is the U.S. national phase entry under 35 U.S.C. § 371 of PCT Application No. PCT/EP2014/071781, filed Oct. 10, 2014, which claims the priority benefit of European Patent Application No. EP2013188236, filed Oct. 11, 2013. Applications PCT/EP2014/071781 and EP2013188236 are incorporated herein by reference in their entirety.

The present invention is related to endoscopic devices for supporting endoscopic surgical tools, and configured for attachment to an endoscope, for use in endoscopic or laparoscopic surgery.

A device of the above kind is known from US 2004/0138682 and is used as an endoscopic suturing device. It comprises a cap assembly that is removably attached to the distal end of an endoscope. The cap has oppositely arranged walls defining a treatment space between them, which is open to the distal end for receiving tissue. A projection extends from a distal end portion of one wall towards the other wall. The projection comprises a bore housing a suturing needle (i.e. the endoscopic tool). The bore communicates with a bore in the connecting wall, which houses a push member for pushing the needle through the tissue that is pulled in the treatment space by a tissue grasping device housed in the endoscope. The opposite wall can comprise an opening for the suturing needle to pass through. A sheath housing a suture thread can be attached to the outside of the opposite wall, such that the suturing needle can engage the suture thread when it passes through the opening.

Another endoscopic suturing device is known from US 2013/0096581. In this case, the needle member is pivotally attached to one wall of a cap assembly which is attached to the distal end of an endoscope. The needle is arched over 90°. When pivoted, it engages axially in an orifice of an opposite wall of the cap after having pierced the tissue. The needle is connected to a pull rod through a gear link which provides for rotational motion of the needle about the pivot.

Yet another endoscopic suturing device is described in US 2005/0251166. This device can be inserted in the lumen of an endoscope and comprises a tissue manipulation assembly pivotally coupled to the distal end of a flexible catheter body. The tissue manipulation assembly comprises pivotally coupled lower and upper jaw members which co-operate to grasp tissue. A flexible launch tube is pivotally coupled to the upper jaw member. The launch tube is slidably held in the catheter and is configured for articulating the jaw members between an open configuration to receive tissue and a closed configuration to hold the tissue. The launch tube houses a suturing needle which can be launched from a distal end of the launch tube across the upper and lower jaw members.

A drawback of the above apparatuses is that they have a tissue receiving space of limited size. Hence, the thickness of the plies of tissue that can be sutured is limited. In the above first two devices, the cap assemblies need be attached to the endoscope prior to insertion in the body. This limits the size of the cap to the size of the endoscope and of the body lumen (e.g. oesophagus, having a diameter of max. 18 mm) through which the cap and endoscope are inserted. In the above first device, the needle is necessarily flexible, since it must slide through a 90° bent borehole. In the above third device, the suturing needle pierces the tissue at a location corresponding to the grasper. The suture is therefore necessarily located very close to the fold of the tissue.

In order to help people lose weight, various surgical procedures have been developed which provide for reducing the size of the stomach. One such group of procedures obtains stomach reduction by forming folds in the gastric wall and suturing the folds independently or to one another. These procedures can be carried out through endoluminal surgery and in such case are referred to as transoral gastric plication or transoral gastroplasty.

However, since the gastric wall is relatively thick and tough, the suturing of the folds results to be a difficult and time consuming task. It would hence be advantageous of being able to make and suture a limited number of large tissue folds instead of a large number of smaller ones. Moreover, when suturing a fold, it is advantageous to make the suture run completely through the plies of tissue forming fold, i.e. in case of gastric plication to make a transmural suture which runs through the gastric wall, as this leads to a better fusion of the plied tissues and hence an improved outcome in the long run. However, in order to do this, the suturing needle must be able to pierce completely through the tissue layers forming the fold. Current devices are however neither capable of suturing large folds at a suitable distance from the edge of the fold, nor are they capable of performing suitable transmural piercings.

An endoscopic accessory surgical tool holder for attachment to an endoscope is described in US 2005/0234297. This device comprises a stationary first body and a second body which is articulately coupled to the first body through a coupler. The first body is formed as a sleeve bracing around the distal end of an endoscope. An accessory channel is attached to the second body and provides a passageway for an endoscopic tool to a treatment space in front of an endoscope. Because the second body articulates relative to the first body, the second body can be manoeuvred in a way that controls the exiting trajectory of the passageway, and hence of the surgical tool held in the accessory channel. A drawback of this device, is that due to the construction of the coupler and the first body, the angle between the exiting trajectory of the passageway and the axis of the endoscope is limited.

Another endoscopic tool holder for attachment to an endoscope is described in WO 2007/104397. It comprises a base structure connected to the distal end of an endoscope. A linkage mechanism formed of two links is connected to a proximal and a distal point of the base structure to form an adaptable triangle with the base structure. A tubular member is connected to the linkage mechanism, such that corresponding portions of the tubular member can be oriented parallel to the links. In this device, the tubular members holding the surgical tools are firmly held by the linkage mechanism and hence can withstand large reaction forces. Also, the exit trajectories of the tubular members can be oriented relative to the axis of the endoscope over a large angular range. However, since the tubular members can only be moved in a plane parallel to the base structure, the base structure actually forms a hindrance to the treatment space, which limits the surgical procedures that are possible with this device.

Yet another endoscopic tool holder for attachment to an endoscope is described in WO 2005/122862. It comprises one or a pair of clamping members for attachment around the distal wall of the endoscope. Flexible tubular members receiving endoscopic tools extend distally from the clamping members to a treatment space ahead of the endoscope. Control wires are attached to the tubular members in order to flex them and provide direct access to the working space from a transverse orientation relative to the endoscope axis. An advantage of this device is that it allows to be assembled to the endoscope inside the patient, hence enabling the creation of larger working spaces. However, the tubular members are too flexible and cannot take up large forces which are required for operating some endoscopic tools (e.g. piercing tissue).

Aspects of the present invention therefore envisage providing devices for supporting endoscopic tools which overcome the above drawbacks. Aspects of the present invention aim at providing devices for supporting endoscopic tools which provide for a larger treatment or working space for the endoscopic tool. Aspects of the present invention aim at providing devices for supporting endoscopic tools which provide an improved rigidity in supporting the tool and/or increased versatility in orienting the tool. Aspects of the present invention aim at providing devices for supporting endoscopic tools which allow for using tools which can be rigid over a greater length at the distal tip, such as needles having a longer rigid distal tip. Aspects of the present invention also aim at providing such devices for supporting endoscopic tools which are of simple construction.

According to the invention, there is therefore provided a device (assembly or apparatus) for supporting an endoscopic tool, which comprises attachment means (or an attachment device) for attaching the device to an endoscope, a first guide tube with a distal open end and configured for accepting and advantageously guiding the endoscopic tool, and first and second projecting members extending distally of the attachment means. When the device is attached to the endoscope, the projecting members are spaced apart, advantageously in a facing relationship, to define a working or treatment space between them.

According to an aspect of the invention, the attachment means comprise first and second clamping members, advantageously arranged in a facing relationship, and at least one cable linking the clamping members. The cable advantageously extends proximally of the clamping members to an operator's position. The cable is remotely actuatable for moving the clamping members relative to each other to adjust a spacing between the clamping members. The spacing advantageously allows an endoscope to be inserted between the clamping members. The cable can be locked for holding the clamping members in a clamping position when the endoscope is inserted between the clamping members, to secure the clamping members to the endoscope. In other words, the clamping members are configured to move relative to each other upon remote actuation of the at least one cable, such that a spacing between the clamping members is adjusted. Remote actuation of the cable advantageously allows for moving the clamping members between different positions, being:

(i) a closed position corresponding to a configuration wherein the spacing is minimal and the clamping members provide minimal bulkiness,
(ii) an open position wherein the spacing is such that an endoscope can be inserted through the spacing, and
(iii) a clamping position wherein the spacing is such that (a lateral wall of) the endoscope can be clamped between the clamping members.

According to an aspect of the invention, the first projecting member is attached to the first clamping member such that it has a fixed or at least one fixable position relative to the first clamping member. Advantageously, the second projecting member is attached to the second clamping member such that it has a fixed or at least one fixable position relative to the second clamping member. The first and the second projecting members, which extend distally from the clamping members, are spaced apart when the clamping members are in the clamped position. In the present invention, the term position can refer both to a (linear) translational position, or an angular orientation. The above hence means that at least the first projecting member, and additionally, or alternatively, the second projecting member can have none, one or more degrees of freedom relative to the corresponding clamping members, which degrees of freedom are furthermore fixable in at least one position or orientation. The first, and possibly the second projecting members are advantageously rigid members.

Since the projecting members extend from the clamping members, and the latter ones are positioned laterally of an endoscope when in a working configuration (i.e. the clamped position), a larger (wider) working or treatment space is obtained compared to prior art devices. Furthermore, the size of the working space is not restricted by the size of the body cavities, since the devices of the invention are capable of being clamped to an endoscope in situ. In other words, actuation of the clamping members via the linking cable makes it possible to insert a device of the invention and an endoscope consecutively in the patient, without the two being assembled to each other, and to secure the device of the invention to the endoscope (via the clamping of the clamping members) at the location of surgery inside the patient. As a result, a larger working space is created by a co-operation of the clamping members and the projecting members.

According to yet another aspect of the invention, the first guide tube is slidable relative to the first clamping member. Furthermore, the distal end of the first guide tube is pivotally attached to a distal end of the first projecting member. By sliding the first guide tube relative to the first clamping member in a distal direction, the first guide tube is made to assume an S-shape configuration, wherein the distal end assumes an orientation transverse and advantageously substantially perpendicular to the first projecting member.

According to yet another aspect of the invention, the distal end of the first guide tube is in communication with the working space when in the transverse orientation. In this position of the guide tube, the endoscopic tool received in it can be moved across the working space.

Hence, since the first projecting member can be fixed in at least one position relative to the clamping member, it forms an advantageously rigid framework for firmly supporting the guide tube and endoscopic tool accommodated therein. Furthermore, the pivotal and slidable arrangement of the guide tube to the clamping and projecting members allows for positioning its distal end in a wide range of orientations. Due to the (rigid) framework obtained by the clamping and projecting members, a firm positioning of the guide tube is advantageously obtained in each and every of the possible orientations. First of all, this is advantageous, since it allows the endoscopic tool for being firmly supported, despite a possibly long lever arm of the projecting member. Consequently, it also allows a large force to be exerted by the endoscopic tool in the working space, since the fixedly (or fixably) positioned first projecting member allows for absorbing the reactive force. Secondly, the combination of features is particularly advantageous when tissue must be drawn in it, or when the surrounding tissue must be protected from the working space.

A first advantageous application of devices of the invention is for endoscopic suturing folds in the gastric wall, e.g. for obtaining stomach reduction. Since the working space in devices of the invention is made large, this is particularly suitable for accepting folds of the gastric walls, which can subsequently be pierced transmurally (i.e. completely through the gastric wall) by a suturing needle housed in the first guide tube. The fixable projecting members allow for exerting large piercing forces. The pivotal and slidable guide tube allows for using needles with a longer rigid distal tip—i.e. stronger needles—to effectively make the transmural sutures.

A second advantageous application of devices of the invention is for mucosectomy. In this case, the second projecting member can act as a shield to protect healthy muscular layer from being damaged, while the guide tube and the first projecting member co-operate to house a grasper for lifting the dissected mucosa. In this case, the larger working space obtained by the clamping members, together with the fact that the distal end of the guide tube can be oriented allow for greatly easing the lifting operation and/or lifting the dissected mucosa over a larger height.

Advantageous aspects of the present invention are set out in the dependent claims.

Aspects of the invention will now be described in more detail with reference to the appended drawings, which are illustrative only and wherein same reference numbers illustrate same features and wherein.

In describing the present invention, the terms distal and proximal are used according to the customary practice in the field of endoluminal or minimally invasive surgery. Therefore, the term distal as used herein refers to a direction away from, or at an opposite end of the location where the surgeon operates the medical devices, such as an endoscope. The term proximal as used herein refers to a direction towards or at the location where the surgeon operates the medical devices.

In describing the present invention, the term axial, unless otherwise indicated, refers to a direction along the projecting members, i.e. a direction across the working space defined by the device of the invention, from the proximal end to the distal end or vice versa.

Figure 1:
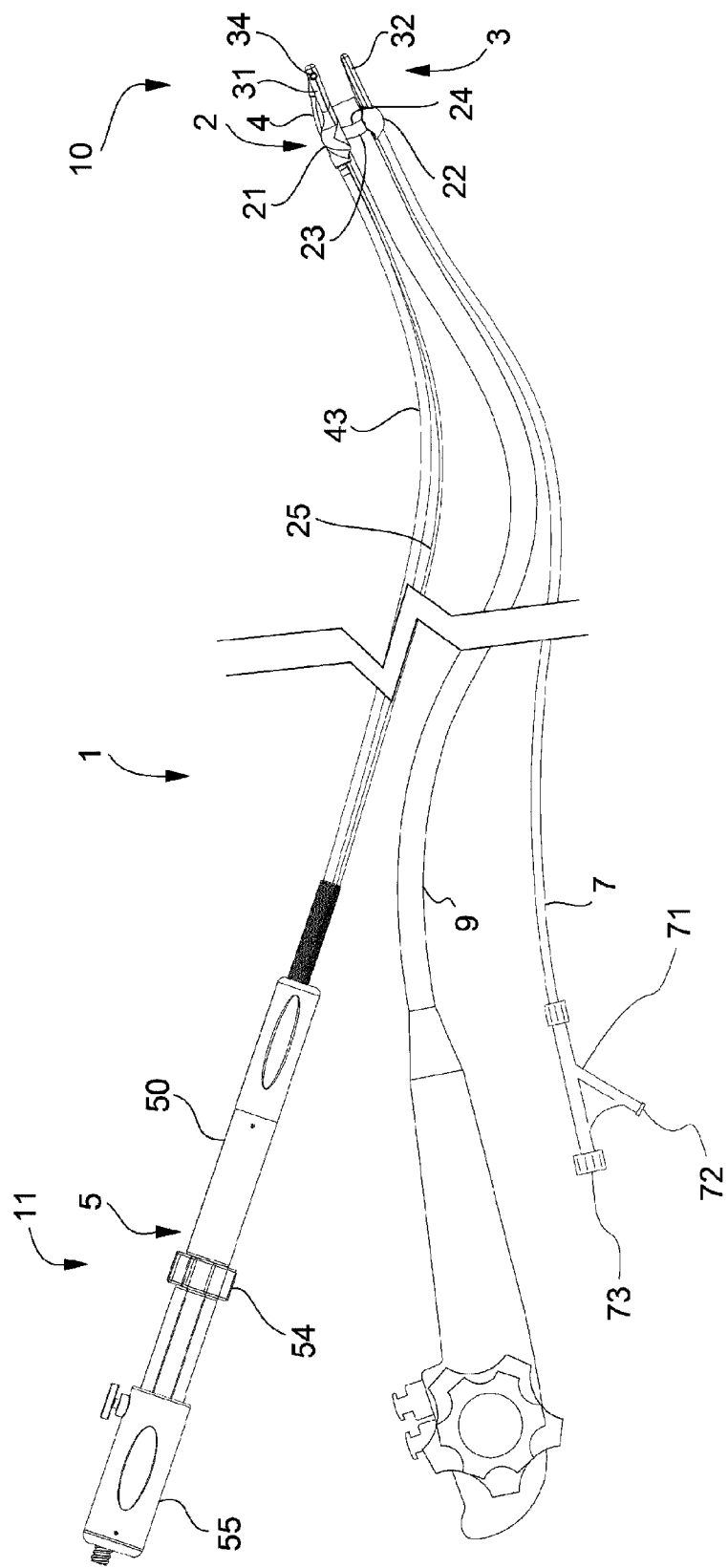
FIG. 1 represents a device according to the invention when assembled (clamped) to an endoscope.

Referring to FIG. 1, devices 1 for supporting endoscopic tools according to the invention comprise endoscope attachment means 2, an arrangement 3 of projecting members, and a first guide tube 4, all of which are provided at a distal end 10 of the device 1. To operate the device 1, control means 5, which may form an integral part of the device 1, are advantageously provided at a proximal end 11 of it.

Figure 2:
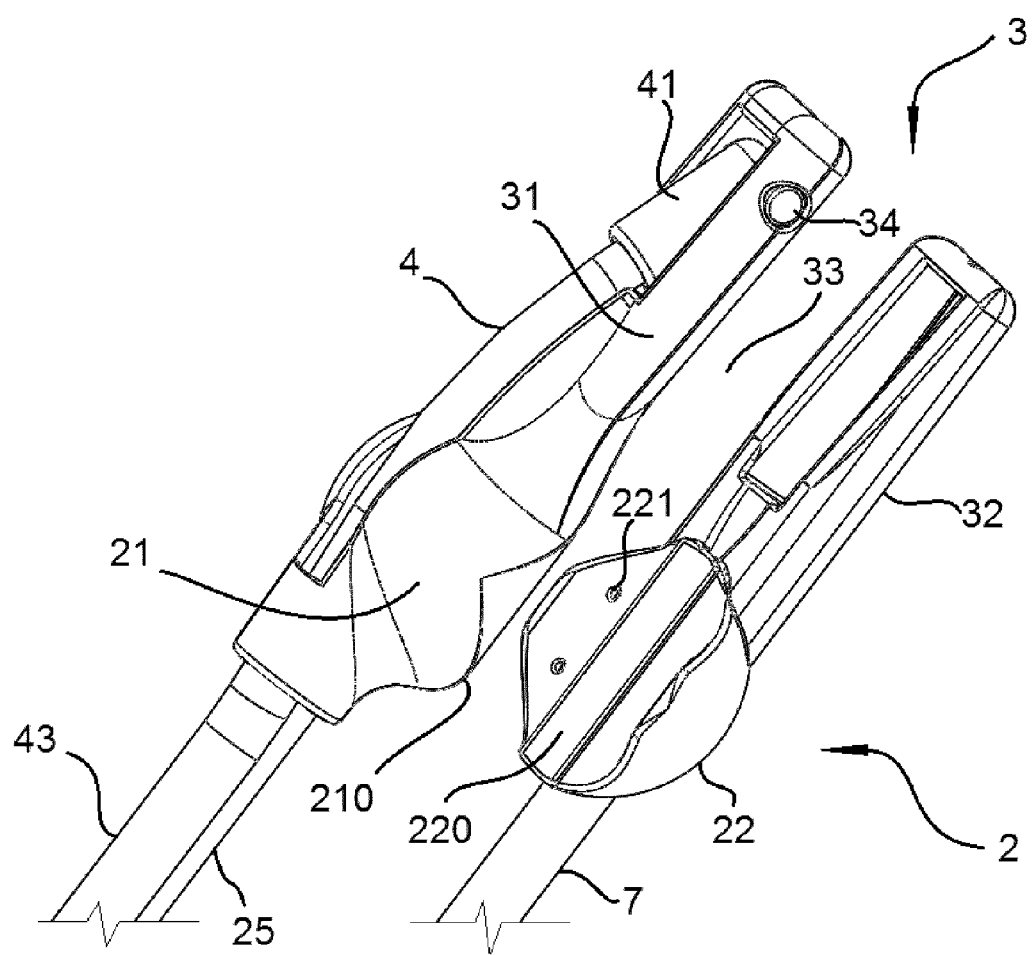
FIG. 2 represents a perspective view of the distal end of the device of FIG. 1.

The distal end 10 of device 1 is shown in greater detail in FIG. 2. The attachment means 2, which are configured for remote attachment of the device 1 to an endoscope 9, comprise two separate clamping members: a first clamping member 21, and a second clamping member 22, disposed in facing relationship to each other. More clamping members may be provided if desired. Advantageously, at the sides facing each other, the clamping members 21, 22 have surfaces 210, respectively 220 which are advantageously shaped to fit around (the wall of) an endoscope 9. By way of example, as shown in FIG. 2, inner surfaces 210, 220 can have a concave shape.

The clamping members 21 and 22 are linked by one or more cables. In the device of FIG. 1, two cables 23 and 24 are provided for linking the clamping members.

Figure 3:
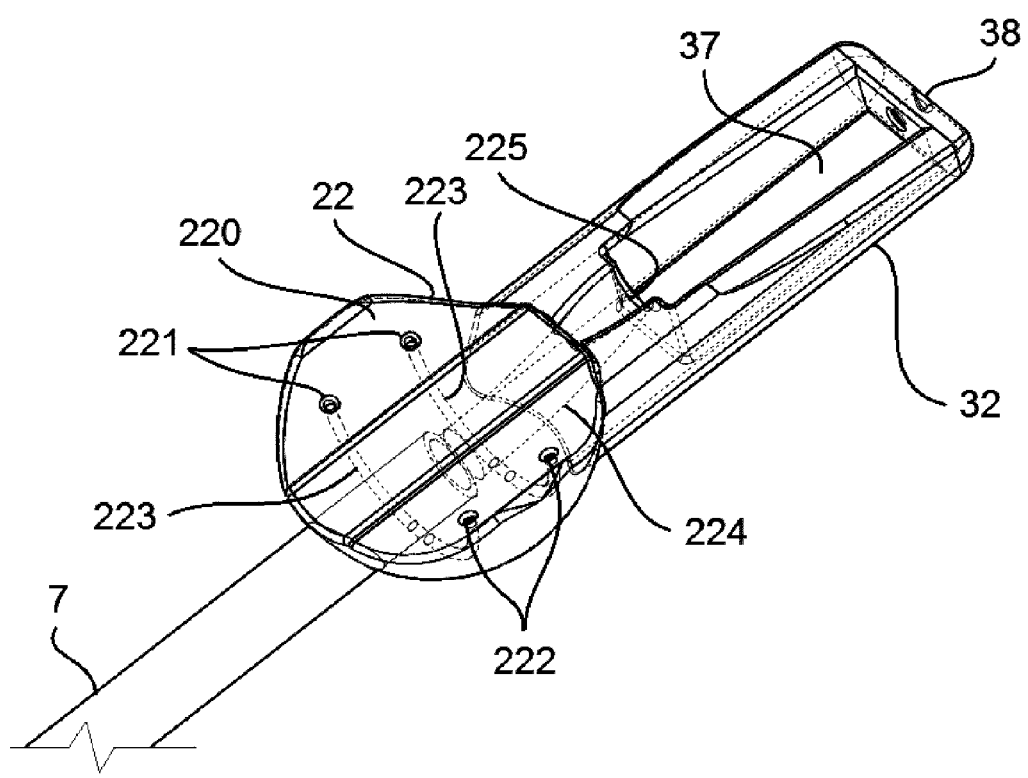
FIG. 3 represents a perspective view of the second clamping and projecting members of the device of FIG. 1.

As shown in FIG. 3, the second clamping member 22 comprises two pairs of cable ports 221 and 222. Cable passages 223 connect the ports 221 of the first pair to corresponding ports 222 of the other pair. Cable passages 223 guide the cables 23, 24 through the clamping member 22, and are advantageously formed as ducts or channels, at least a portion of which is arranged in the interior of clamping member 22, i.e. the cable passages 223 are advantageously at least in part formed as a closed channel (i.e., a channel having a closed cross section), such that the cables 23 and 24 are attached or linked to the clamping member and so as to prevent the cables slipping out of the channels.

Figure 4:
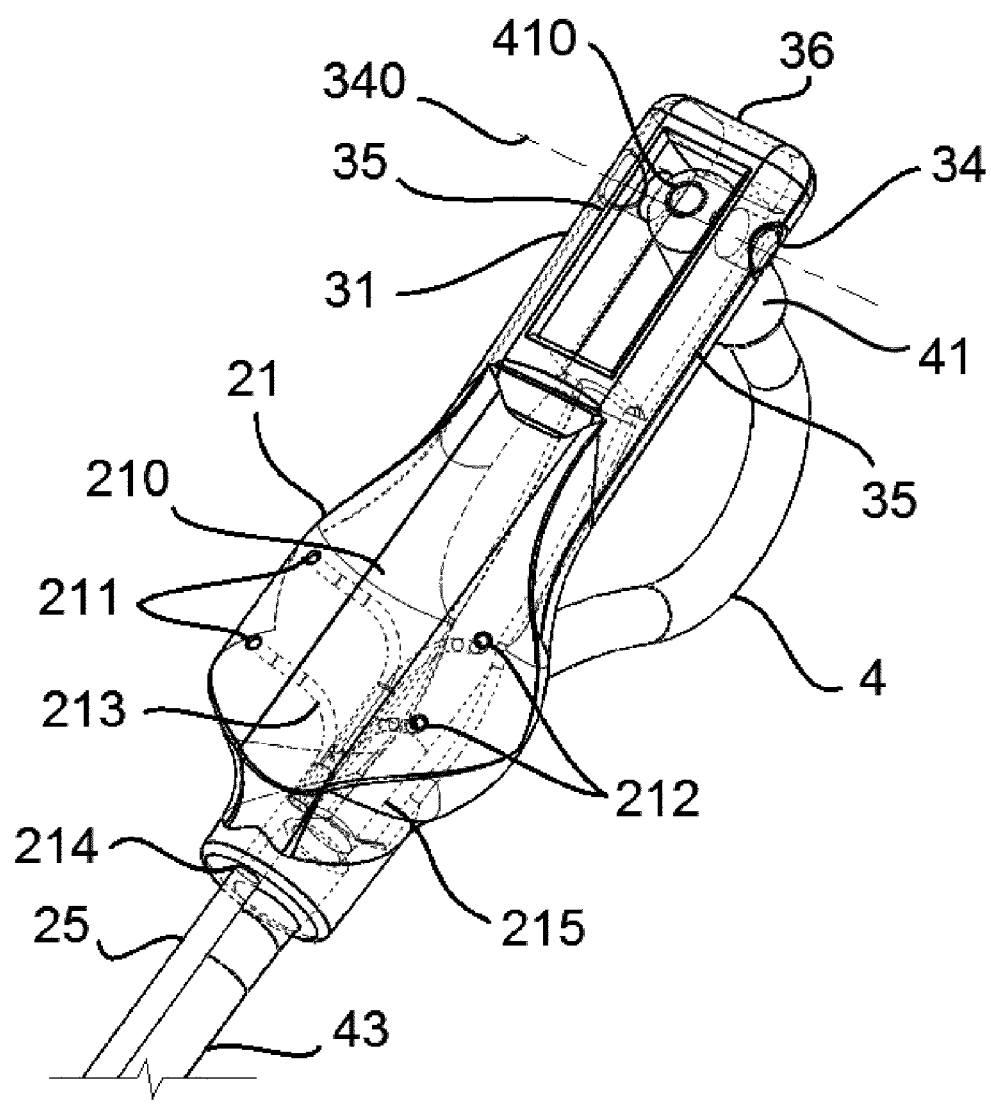
FIG. 4 represents a perspective view of the first clamping and projecting members of the device of FIG. 1.

Cables 23 and 24 further extend between the second clamping member 22 and the first clamping member 21. As shown in FIG. 4, the first clamping member 21 comprises two pairs of cable entry ports 211 and 212 which correspond to the cable ports 222 and 221 of the second clamping member 22 shown in FIG. 3. Cable passages 213 in the first clamping member 21 connect the four cable ports 211, 212 to an exit port 214 in the first clamping member. The exit port 214 is in turn connected to the proximal end 11 of device 1 via a cable duct 25.

Cables 23 and 24 are inserted in the cable passages 223 of the second clamping member 22, such that each cable enters one passage 223 through a port 221 of the first pair and exits the passage 223 through the corresponding port 222 of the other pair. By so doing, each cable forms a loop running through the second clamping member 22. Cable portions exiting each port 221, 222 of the second clamping member 22 enter a corresponding port 212, 211 of the first clamping member 21, from where they are guided through cable passages 213 to exit port 214. Hence, a total of four cable ends (two end portions of each cable 23, 24) run through exit port 214, and from there, through cable duct 25 to the control means 5 at the proximal end 11. It is possible to merge the four cables into a single thicker wire proximally of exit port 214 for increased strength.

The arrangement of cables 23, 24 described above allows for moving the second clamping member 22 towards, or away from, the first clamping member 21 by pulling, respectively pushing all four cable ends. Advantageously, the actuation of the cables (i.e. pushing or pulling) is effected simultaneously. It can advantageously be effected at a remote location (proximally), through a control handle 5 as will be described further below.

Moving the clamping members 21 and 22 away from each other allows for increasing the spacing between them to obtain an open position, wherein the spacing between the clamping members is such that an endoscope 9 can be inserted between the clamping members 21 and 22. It will be convenient to note that the two pairs of cable ports 211 and 212 should be arranged at a sufficient distance from each other in order not to hamper insertion of the endoscope 9. Same applies to the cable ports 221 and 222 on the second clamping member.

Once a distal portion of the endoscope 9 is located between the clamping members 21 and 22, the ends of cables 23 and 24 can be pulled advantageously simultaneously to bring the clamping members towards each other and reduce the spacing between them. As a result, the clamping members 21, 22 will engage with their inner surfaces 210, respectively 220 an outer wall of the endoscope 9 to provide a tight clamping. By maintaining the cables in the latter pulled position, it is obtained that the distal end 10 of device 1 is secured to the endoscope 9 through clamping members 21, 22.

It will be convenient to note that the above operation can be obtained through the use of only one cable instead of the above two, even though two cables will provide improved motion stability. Alternatively, the two attachment cables 23, 24 can be replaced by a set of four cables, which pass through cable passages 213 in the first clamping member 21 and are attached with one end to a cable port 221 or 222 of the second clamping member 22. This arrangement hence differs from the two cable arrangement as described above in that the four cables do not form a loop through the second clamping member 22, but each cable has one end secured to it.

Figure 5:
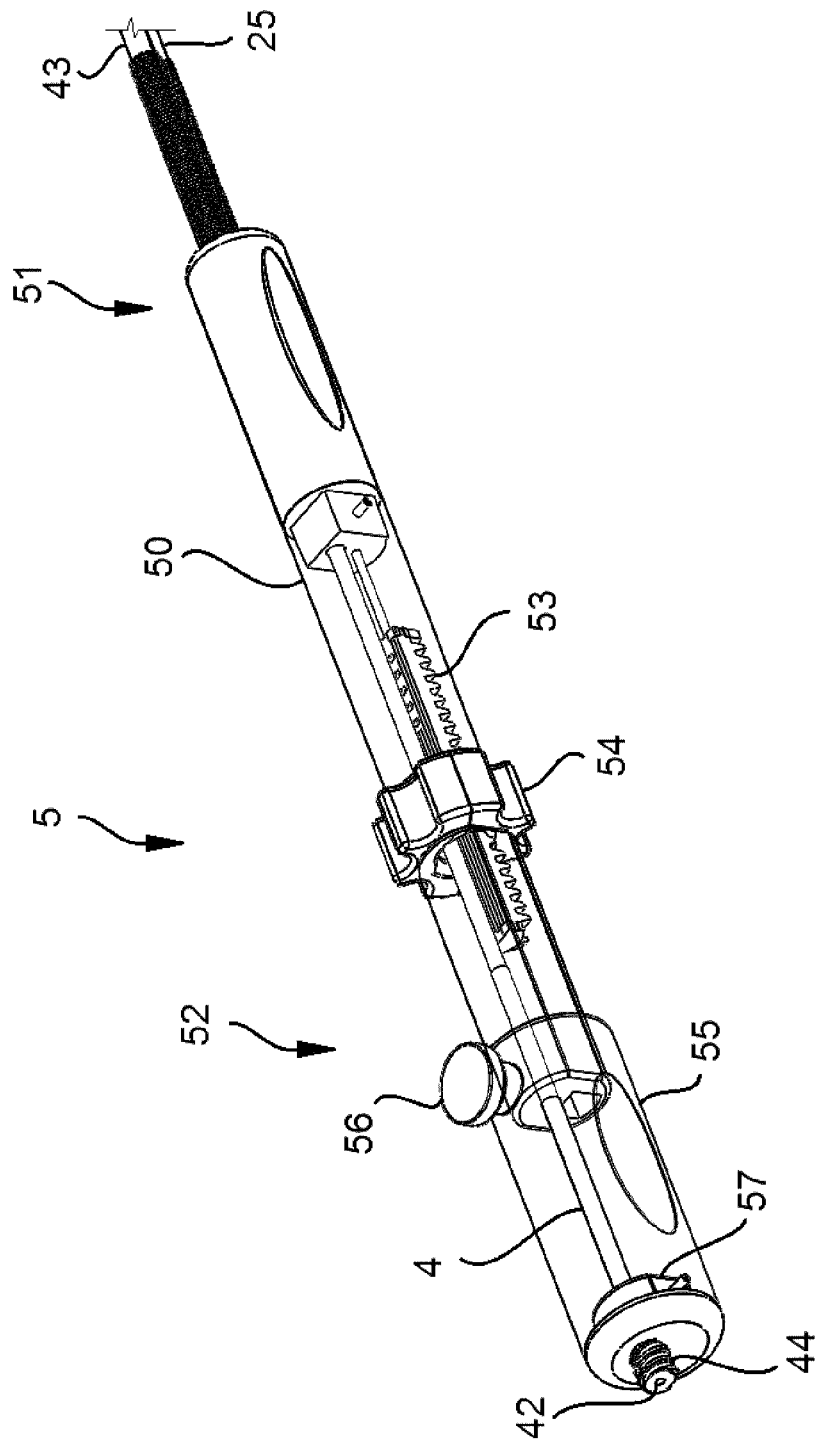
FIG. 5 represents a perspective view of the control handle of the device of FIG. 1, wherein the housing 50 and sleeve 55 are drawn in transparency to view the inside.

Operation (or actuation) of the cables 23, 24 is advantageously performed at a proximal end 11 of the device through a control handle 5, which advantageously comprises an actuator being able to move the attachment cables 23 and 24 relative to the cable duct 25. A possible actuator is shown in FIG. 5. Hence, cable duct 25 extends between the first clamping member 21 and the control handle 5 and guides the four ends of cables 23, 24 to the control handle 5. The control handle 5 comprises an advantageously elongate housing 50 having a distal end 51 and a proximal end 52. The proximal end of the cable duct 25 is secured to the housing, such as at distal end 51. The ends of cables 23 and 24 extend proximally of the cable duct 25 and are secured to a rack 53 which is arranged slidable relative to housing 50. Rack 53 is advantageously housed inside housing 50.

A control ring 54 having an internal worm gear is provided on the housing 50 so as to mesh with the rack 53. Control ring 54 advantageously fits in a recess (not shown) provided in housing 50 which locks all degrees of freedom of control ring 54 other than a rotation on an axis parallel to rack 53. As a result, by turning control ring 54, rack 53 is made to slide relative to the housing 50 and to cable duct 25.

By so doing, it is possible to operate the clamping members 21, 22 from a remote location. It will be convenient to note that suitable actuators other than the rack and worm gear, such as e.g. pneumatic actuators can be used to provide sliding motion of the attachment cable ends relative to cable duct 25 and hence the clamping member 21.

It is possible to lock the control ring 54 in a specified rotational position relative to the housing 50 by means as known in the art, such as a set screw.

Now that the remote actuation of the clamping members 21 and 22 has been described, it will be readily apparent that it is advantageous to shape the clamping members such that they are compact in height, which term refers to a linear dimension along the axis of the endoscope over which the clamping member engages the endoscope when in a clamped position. The height of the clamping members advantageously is smaller than or equal to 50 mm, advantageously smaller than or equal to 40 mm, advantageously smaller than or equal to 30 mm, advantageously smaller than or equal to 25 mm. Such a small clamping member preserves the flexibility of the endoscope, in particular at the distal end, so that endoscope positioning during minimally invasive surgery is not hampered. This is important, since most of the endoscope's angulation happens at the distal end.

In order to facilitate insertion of devices of the invention in a patient, the clamping members 21, 22 can be moved against each other by actuation of the attachment cables 23, 24 and be held in that position which corresponds to a configuration wherein the spacing between the clamping members is minimal (or none at all) and the clamping members assume a minimal bulkiness (i.e. a maximal compactness). The latter position is referred to as the closed position of the clamping members. Compact clamping members facilitate remote (i.e. in situ) mounting of the device to the endoscope. Hence, devices of the invention are advantageously inserted in a patient, either endoluminally or laparoscopically, when they are not yet attached to the endoscope. Advantageously, in the closed position, the clamping members assume an overall size such that the smallest circumscribing cylinder has a diameter smaller than or equal to 26 mm, advantageously smaller than or equal to 21 mm, advantageously smaller than or equal to 18 mm. This avoids unintended perforation or laceration of the body cavity through which devices of the invention are inserted, such as the oesophagus.

Referring again to FIGS. 1 and 2, devices 1 of the invention comprise an arrangement 3 of projecting members extending distally from the clamping members. The arrangement advantageously consists of a pair of projecting members 31, 32, but more projecting members can be provided as desired. In what follows, the projecting members 31, 32 will be referred to as brackets.

Hence, a first bracket 31 extends from the first clamping member 21 in a distal direction. In facing relationship thereto, there is provided a second bracket 32, extending from the second clamping member 22. According to the invention, the position (orientation) of each bracket relative to the corresponding clamping member is either fixed, or variable. In the latter case, each bracket can be fixed in at least one position (orientation) relative to the corresponding clamping member.

FIGS. 1 and 2 represent an embodiment wherein brackets 31 and 32 are fixedly secured to and advantageously formed integrally with corresponding clamping members in a non-adaptable position/orientation. At least the first bracket 31, and possibly the second bracket 32 as well, are advantageously rigid (i.e. they are not flexible), at least when assuming the fixed or fixable position.

When the device 1 is in a clamped position with the clamping members 21, 22 clamped on the endoscope 9, the brackets 31, 32 are spaced apart to define a working space 33 between them, which is distally open. The working space is proximally delimited by the endoscope 9. Brackets 31, 32 can advantageously extend substantially parallel to each other. Alternatively, they can extend obliquely, such that they are further distanced apart towards the distal direction.

The distal end 41 of a guide tube 4 for supporting an endoscopic tool is pivotally attached to the first bracket 31. To this end, the first bracket 31, which extends from the first clamping member 21, is provided with a pivot 34 disposed at a distal end of the bracket. Referring to FIG. 4, pivot 34 advantageously has an axis of rotation 340 extending transverse and advantageously (substantially) perpendicular to the proximal-distal (axial) direction. Pivot 34 is supported by, and extends between two oppositely arranged legs or uprights 35 of bracket 31. Bracket 31 is open between legs 35. The distal end 41 of the guide tube 4 is attached to pivot 34 such that it is interposed between legs 35 of the first bracket 31. Distal end 41 is hence configured to rotate about pivot axis 340.

A passage 215 for the guide tube 4 is provided through the first clamping member 21, in which guide tube 4 is slidably held. Passage 215 can be at least partially formed as a closed channel to prevent the guide tube 4 from slipping out. Guide tube 4 further extends from the passage 215 to a proximal end 42 at the proximal end 11 of device 1. The guide tube 4 is advantageously housed in a guide tube duct 43 extending between passage 215 and the proximal end 11 of the device 1 for protecting the guide tube 4 inside the patient and for enabling to easily slide the guide tube and hence pivot the guide tube 4 on pivot 34 as is described below. Possibly, guide tube duct 43 and cable duct 25 can be merged in a multilumen tube.

Figure 6:
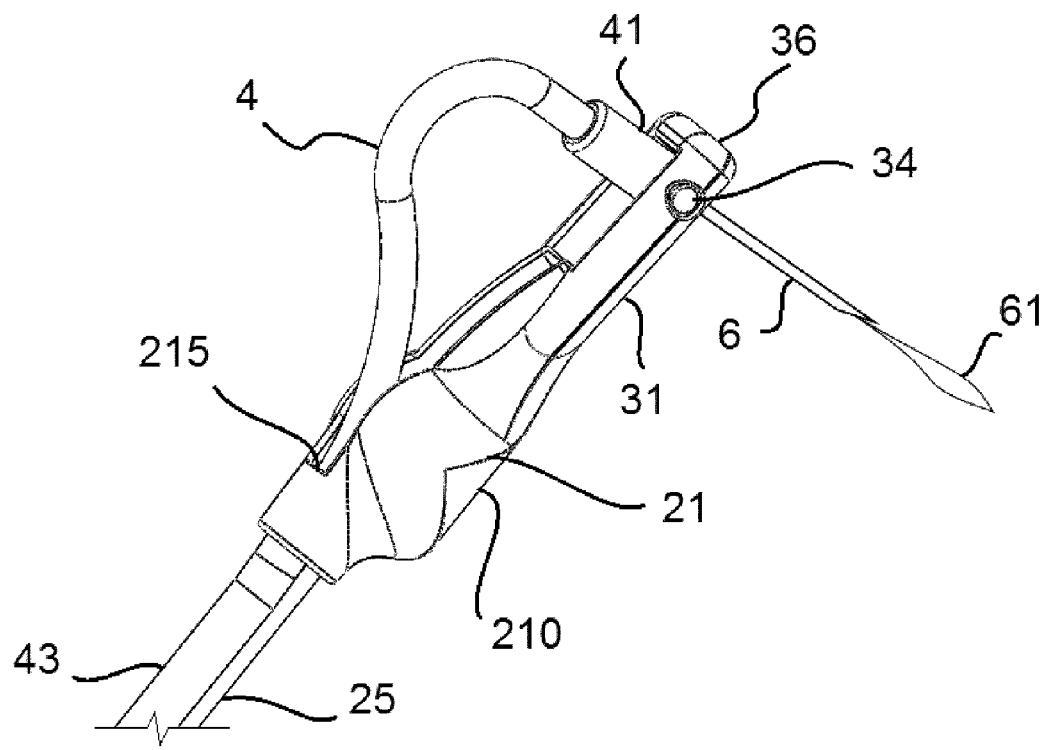
FIG. 6 represents yet another perspective view of the first clamping and projecting members of FIG. 1.

The guide tube 4 is open both at the distal end 41 (opening 410) and at the proximal end 42 in order to insert an endoscopic tool through it. Guide tube 4 has a flexible portion extending distally, advantageously at least between the guide tube passage 215 and the distal end 41. The flexible portion enables to rotate the distal end 41 of the guide tube 4 about pivot 34, between a retracted position, as shown in FIG. 2, wherein the guide tube 4 is substantially tensed between distal and proximal ends, and a flexed position, as shown in FIGS. 4 and 6, wherein the guide tube 4 is flexed between guide tube passage 215 and pivot 34 to assume an S-shape. In the retracted position, the guide tube 4 assumes a minimal bulkiness (minimal volume) to facilitate endoluminal insertion. In this position, the guide tube is advantageously as straight as geometrical constraints permit, with distal end 41 being suitably substantially parallel to bracket 31.

The transition from the retracted position to the flexed position of the guide tube and vice versa is obtained by sliding the guide tube 4 through duct 43 and relative to the clamping member 21 and bracket 31. Pushing the guide tube through duct 43 and guide tube passage 215 will make the distal end 41 of guide tube 4 rotate about pivot 34 such that the guide tube assumes an S-shape between passage 215 and pivot 34. Advantageously, devices of the invention allow for flexing the guide tube such that the distal end 41 of guide tube 4 can assume an orientation substantially perpendicular to the bracket 31, as shown in FIG. 6.

Since the guide tube is slidably and pivotally attached to a rigid framework formed by the first clamping member and the first bracket, an assembly is obtained which does not deflect when large forces are exerted by the endoscopic tool, which is housed in guide tube 4, on the body (tissue). This advantage will become evident when an application for endoscopic suturing will be described further below.

Advantageously, the guide tube 4 is actuated (pushed) remotely to assume the flexed position. To this end, the proximal end 42 of the guide tube 4 is advantageously operated by control handle 5. Referring to FIG. 5, control handle 5 advantageously comprises a sleeve 55 slidably arranged over housing 50. Guide tube duct 43 is secured to housing 50, such as at the distal end 51. Guide tube 4 extends slidably through the housing 50 until proximal end 42, where it is secured to sleeve 55. By sliding sleeve 55 relative to housing 50 and hence guide tube duct 43, the guide tube can be pushed proximally to distally assume the flexed position. A set screw 56 allows for fixing sleeve 55 relative to housing 50 in the desired position and hence for fixing the guide tube 4 in the distal configuration.

The guide tube 4 can have a proximally extending rigid portion to prevent buckling of the guide tube 4 when pushing it. Another possibility is to use a guide tube duct 43 having an internal diameter slightly larger than the diameter of the guide tube 4, so that duct 43 prevents buckling of the guide tube 4.

Advantageously, as shown in FIG. 6, the first bracket 31 can be provided with a stop member 36 configured as abutment for the distal end 41 of the guide tube 4 when in the maximal flexed position. Stop member 36 can be formed as a connecting bracket between the legs 35 of the first bracket 31. In the flexed position, the stop member 36 can aid in stabilising the orientation of the (distal end of the) guide tube and hence of the endoscopic tool housed in it. Alternatively, or in addition, the stop member 36 forms a cap which closes the distal end 41 of the guide tube 4 when in the retracted position to prevent the endoscopic tool housed in it from slipping out, or to prevent ingress of bodily liquids in the guide tube, as shown in FIG. 2.

Figure 18:
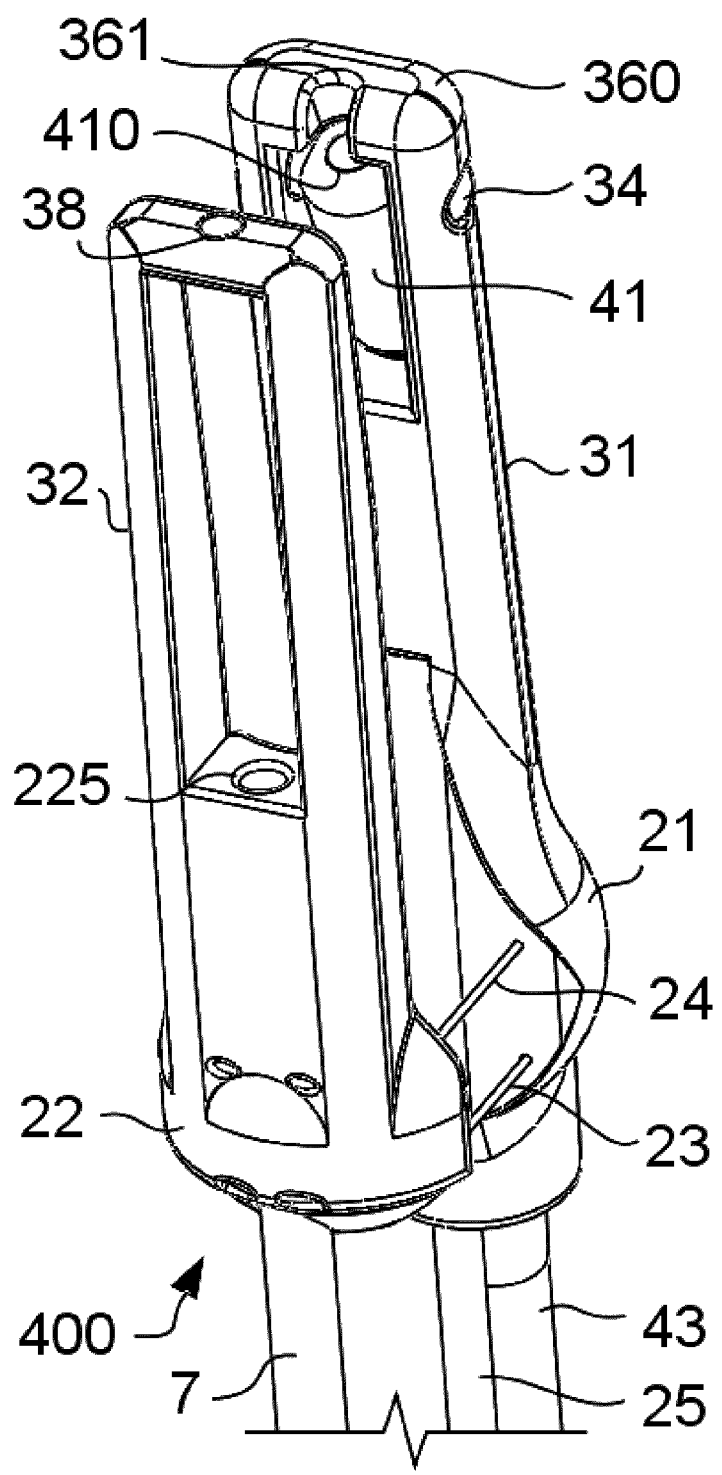
FIG. 18 represents a perspective view of the clamping members and projecting members of yet another embodiment of a device according to the invention.

Alternatively, it may be advantageous keep distal opening 410 of guide tube 4 free from obstruction in the retracted position of the guide tube. Referring to FIG. 18, endoscopic support device 400 differs from device 1 of FIGS. 2-4 only in the shape of the stop member. Stop member 360 of FIG. 18 is shaped to keep the distal opening 410 of the guide tube clear from obstruction, even when the guide tube is in the retracted position (i.e. substantially parallel to projecting member 31). To this end, stop member 360 comprises an aperture 361 at a location corresponding to the distal opening 410 to provide clearance for an endoscopic tool, such as a suturing needle, such that the tool can at least partially project from end 410. Keeping distal end 410 of guide tube 4 clear from obstruction when in the retracted position prevents damage to the endoscopic tool (e.g. a suturing needle) when the tool is inadvertently moved past distal end 410 and against the stop member 36. This can happen when there is no accurate record of the tool's position along the guide tube. Another advantage is that, where there is no accurate record of the tool's position along the guide tube, making the tool project from the opening 410 enables to see the tool with an endoscopic camera and to ascertain its correct position. If the (rigid) tool would unknowingly be in a too proximal position in the guide tube, this would hinder flexing the guide tube. Hence, flexing the guide tube is made easier. Yet another advantage, is that aperture allows for using even longer rigid tools (e.g. needles) than the flexible guide tube alone would permit. Indeed, aperture 361 allows for moving a suturing needle, or other endoscopic tool, at least partially past distal opening 410 of the guide tube before flexing the guide tube, i.e. before turning the distal end 41 on pivot 34. Arrangements with stop member 360 as in FIG. 18 would allow for using rigid needles up to 30 mm length, whereas arrangements as in FIG. 4 would allow rigid needles up to about 20 mm length.

Advantageously, the distance over which guide tube 4 can be flexed, between pivot 34 and passage 215, is at least 15 mm, advantageously at least 25 mm, which enables for using longer suturing needles in the guide tube 4.

To ascertain when the guide tube 4 has assumed the flexed configuration, a stop member 57 can be provided at the proximal end of sleeve 55. Stop member 57 stops advancement of the sleeve 55 and hence tube 4 when a final, flexed configuration has been reached. Additionally, or alternatively, an abutment flange or thickened portion can be provided on the guide tube 4 proximally of passage 215 of the first clamping member 21. By dimensioning the flange to have a size larger than the passage 215, it can act as a stop member for stopping sliding motion of the guide tube. The flange can then be disposed at a position along the guide tube such that the maximal flexed position is obtained when the flange abuts against passage 215.

As an advantage, the guide tube 4 can be locked in any intermediate position between the retracted and the flexed positions, such as by means of set screw 56. This gives devices of the invention a suitable manageability in positioning endoscopic tools despite the rigid framework formed by the bracket and clamping member.

Referring to FIG. 3, the second clamping member 22 can be provided with a through-passage 224 extending along the proximal-distal direction and communicating at the distal end 225 with the working space 33. A connecting tube 7 connects the through-passage 224 to the proximal end 11 of the device. Through-passage 224, as well as connecting tube 7, can be sized to accommodate a further endoscopic tool and give it access to the working space 33.

Either the first bracket 31, or the second bracket 32, or both can be provided with a guiding hole 38 for a guide wire, allowing the blind insertion of the device 1 over a standard guide wire. A guide wire can be inserted in the patient with the aid of an endoscope first. The endoscope is inserted in the patient until the target location. The guide wire is pushed out of a lumen of the endoscope and held in the patient while the endoscope is removed. By so doing, the guide wire provides a direct path for subsequent insertion of the device 1. At the proximal side (outside the patient), the guide wire is inserted through hole 38 and the device 1 is pushed along the guide wire in the patient such that it is guided all the way to the target location. This ensures that the device is correctly inserted in the patient and avoids that it would follow an erroneous path Devices according to the invention can be operated as follows. By means of set screw 56, sleeve 55 of the control handle 5 is locked in a position such that guide tube 4 is in the retracted position. An endoscopic tool is inserted in guide tube 4 through proximal end 42 and pushed until the tool 6 arrives at the distal end 41, without however protruding from distal end 41 of the guide tube 4.

The guide tube 4 can comprise at the proximal end 42 a threaded locking member 44, or any other locking mechanism, in order to attach the endoscopic tool 6 to the handle 5 of the device 1.

Control ring 54 is turned in order to move the clamping members 21 and 22 to the closed position so as to assume a configuration with minimal bulkiness. The overall size of the clamping members in the closed position can be selected such that they fit through the smallest endoluminal passage through which they need be inserted. Since the tubes 25, 43 and 7 have a smaller footprint than the clamping members, they will not hinder afterwards insertion of the endoscope. Hence, device 1 is inserted in the patient (such as with the aid of a guide wire), followed by endoscope 9. Needless to say, during insertion, device 1 is not attached to the endoscope 9. Devices of the invention can be inserted both endoluminally and laparoscopically, and are particularly suitable for surgical applications requiring transoral endoscopy.

Once arrived at the target location in the patient's body, the control ring 54 is turned to move the clamping members 21, 22 apart and create an opening of sufficient size to enable endoscope 9 to be inserted therein. The distal end of endoscope 9 is inserted between the clamping members from the proximal side and moved distally until a desired position. Next, control ring 54 is turned in the inverse direction to move the clamping members 21, 22 towards each other until they clamp the endoscope 9 between them. Control ring 54 can be locked in position, e.g. by a set screw or by friction. By so doing, a working space 33 is created, which is delimited laterally by the brackets 31 and 32, and proximally by the endoscope.

Next, set screw 56 of sleeve 55 is unscrewed and sleeve 55 is moved towards control handle housing 50, which causes guide tube 4 to flex at the distal end, as shown in FIG. 6. Guide tube 4 is flexed until it assumes a desired flexed configuration, such as one in which distal end 41 advantageously abuts against stop member 36. The device 1 is now ready for operation.

It is possible to carry out insufflation with devices of the invention in order to expand workroom at the target location. To this end, a possibly inert and nontoxic gas such as carbon dioxide is insufflated into the body cavity through one of the ducts available in the device 1, such as connecting tube 7 and passage 224, or tube duct 43 and passage 215. By way of example, and referring to FIG. 1, a Y connector 71 can be provided at the proximal end of connecting tube 7, through which gas can be insufflated at port 72, whereas port 73 remains available for insertion of an endoscopic tool. Insufflation by devices of the invention can complement insufflation through an endoscope lumen, which for some applications provides an insufficient gas inflow. This is particularly advantageous in transoral endoscopy, where a low resistance escape route for the gas is available through the oesophagus.

Devices of the invention are particularly advantageously used for endoscopic suturing, in particular for transoral gastric plication. In such cases, the endoscopic tool is a suturing needle 6 as shown in FIG. 6, and the working space 33 is used to accept a tissue fold between brackets 31 and 32.

Tissue can be pulled in the working space 33 by known surgical tissue engagement tools, such as a piercing helix or graspers, which can be provided in a lumen of the endoscope 9. Alternatively, a dedicated duct, such as tube 7, may be coupled to either clamping members 21, 22 for guiding a tissue engagement tool to the working space 33 through an opening (e.g. channel 224) provided in either clamping member or bracket.

In operation, once the clamping members are clamped to the endoscope, the tissue fold is pulled in the working space 33. The guide tube 4 can be pushed to the flexed position before, or after pulling in the tissue fold. A suturing needle 6 is inserted in the guide tube 4 through the open proximal end 42 and advantageously pushed until the distal end 41 when the guide tube is still in the retracted position. Suitably, tool 6 can be arranged at the end of a push tube (not shown) configured for pushing the tool through the guide tube 4. Advantageously, needle 6 is already at the distal end of the guide tube 4 when the guide tube is made to assume the flexed position. This way of operation allows for using longer needles which are more effective in piercing tough and thicker tissue layers.

Possibly, suturing needle 6 remains inside the guide tube 4 and does not project out of opening 410 of distal end 41 until after the guide tube 4 has assumed the flexed position. Stop member 36 can ensure that this is the case by configuring it as a cap which closes off or covers the distal opening 410 of guide tube 4 when the guide tube is in the retracted position. Alternatively, it may be advantageous to make the suturing needle 6 project out from the distal opening 410 of the guide tube 4 before starting to turn distal end 41 on pivot 34 and flex the guide tube, as described above in relation to FIG. 18.

Suturing operation can now begin. The needle 6 is advanced to pierce the tissue folds in receiving space 33. During this operation, second bracket 32 advantageously acts as support for holding the tissue in place.

Any suturing needle as known in the art for minimally invasive surgery can be used in devices of the invention. As shown in FIG. 6, suturing needle 6 can be hollow to accommodate an adjustable hoop member 61 in it. Hoop member 61 can be pushed out of needle 6 to intercept a suture thread provided at the opposite side, i.e. at the side of the second bracket 32, by a suture thread providing catheter 8 which can e.g. be provided through connecting tube 7 shown in FIG. 3.

The second bracket 32 advantageously comprises a through-opening 37 to allow the endoscopic tool (the suturing needle 6) to pass through it when launched from the distal end of guide tube 4. For suturing applications, the distal outlet 225 of channel 224 advantageously has an exit trajectory in (or past) the through-opening 37, which enables the hoop member 61 to intercept the suture thread providing catheter 8. Through-opening 37 is advantageously arranged at a position corresponding to the position of the distal end 41 of guide tube 4 on the first bracket 31 and can be wide enough to accommodate misalignment/flexibility of the endoscopic tool.

Figure 7:
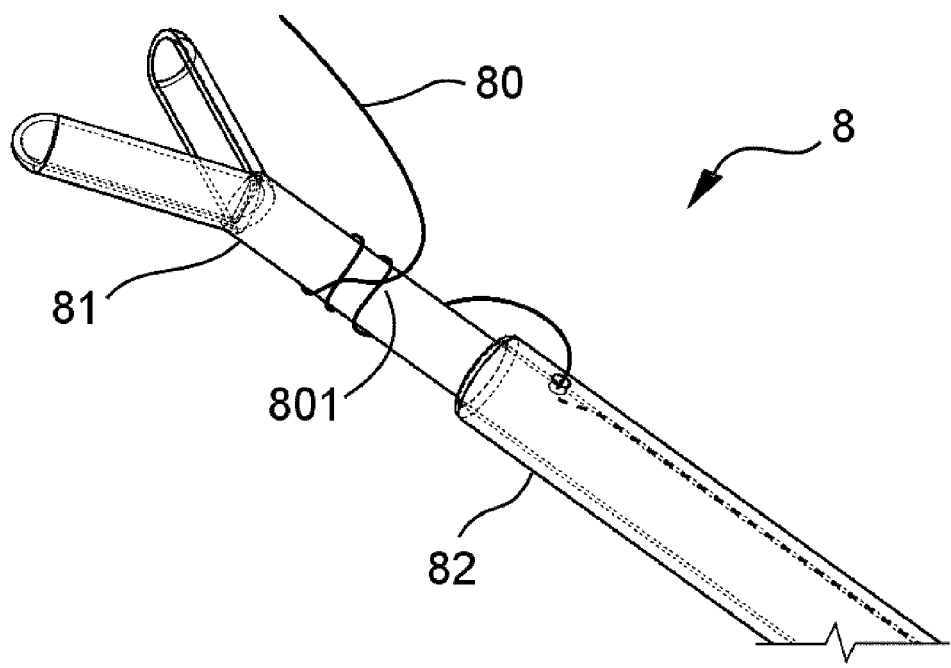
FIG. 7 represents a suture thread providing catheter for use in the device of FIG. 1.

Catheter 8 is shown in FIG. 7, and comprises a thread gripping member 81 arranged at a distal end of the catheter 8 for gripping an end of the suture thread 80. Thread gripping member 81 is slidably arranged in a pushing member 82 shaped as a tube, and which is configured for pushing a pre-tied knot 801 of the suture thread 80 over the thread gripping member 81 in order to fix the suture at the end of a suturing operation. It will be convenient to note that other devices as known in the art can be used as well, for providing same or modified suturing operations.

When the needle 6 arrives at the position of the second bracket 32, after having pierced through the tissue fold, hoop member 61 is advanced out of the needle and pushed in an open configuration. Simultaneously, or consecutively, suture thread providing catheter 8 is inserted through connecting tube 7 to protrude in the through-opening 37 of the second bracket 32. Catheter 8 provides a loose end of a suture thread 80, which is brought through hoop member 61. Hoop member 61 is then closed and retracted within needle 6, which, in turn, can be retracted inside the guide tube 4. By so doing, a first suture thread loop has been created through the tissue. In order to help hoop member 61 engage the suture thread, the clamping members can be released from the endoscope 9 by pushing the linking cables 23, 24, which allows to freely move the endoscope 9 relative to the device 1. By so doing, an assisting endoscopic tool such as a grasper can be launched from the endoscope 9 to intercept suture thread 80 and bring it to hoop member 61.

More thread loops can be created by releasing the tissue fold, repositioning the device 1 and the endoscope 9, and grasping again another tissue fold to repeat the above procedure and bring the suture thread end back to catheter 8. At the end of operation, the pre-tied knot 801 can be pushed over the suture thread 80 to fix the suture loops.

It will be convenient to note that, depending on the particular application, the exit trajectory of the distal outlet 225 of channel 224 can be different. By way of example, the exit trajectory of the outlet 225 can be oblique towards the first bracket, so as to make the endoscopic tool inserted in the tube 7 exit in the centre of the working space 33.

It will be convenient to note that, as already described, the brackets (projecting members) need not be integral with the corresponding clamping member. One or both the brackets can be configured to change position or orientation relative to the corresponding clamping member. However, according to the invention, the bracket must be advantageously rigid and fixable in at least one position or orientation in order to provide for the advantages of the invention.

Figure 8:
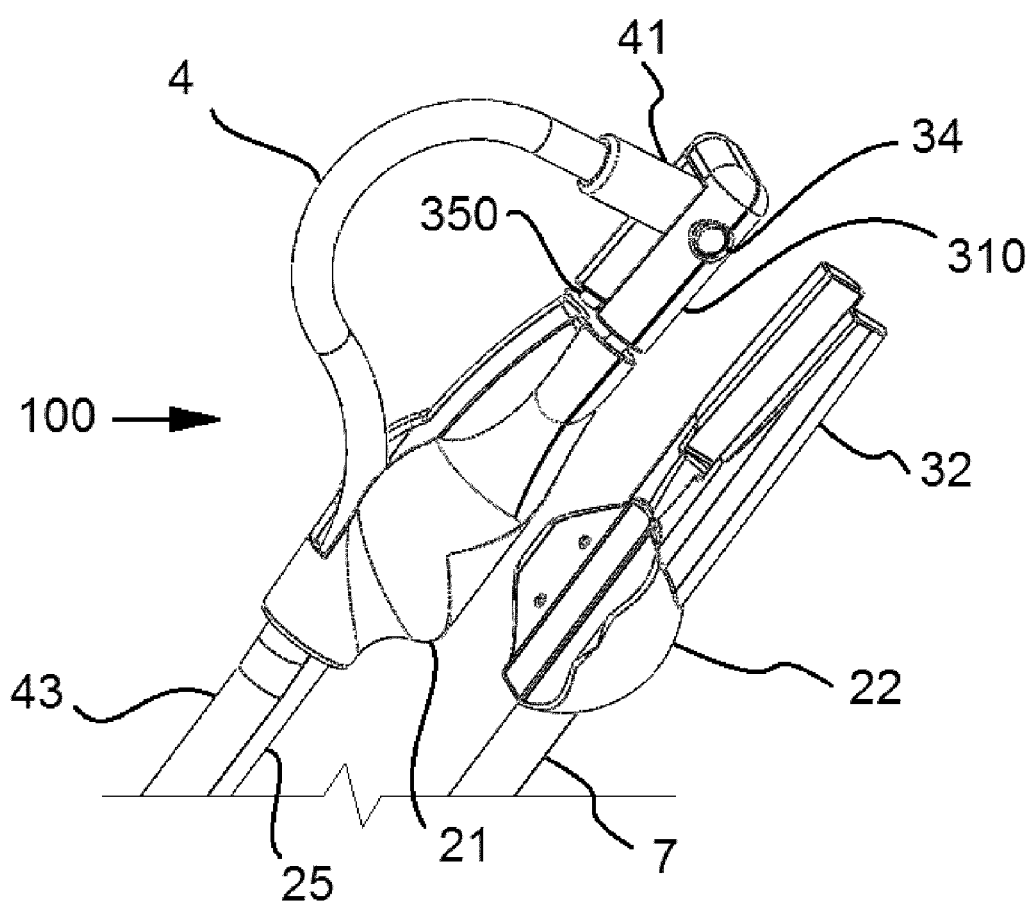
FIGS. 8 and 9 represent perspective views of the distal end of another embodiment of a device according to the invention.
Figure 9:
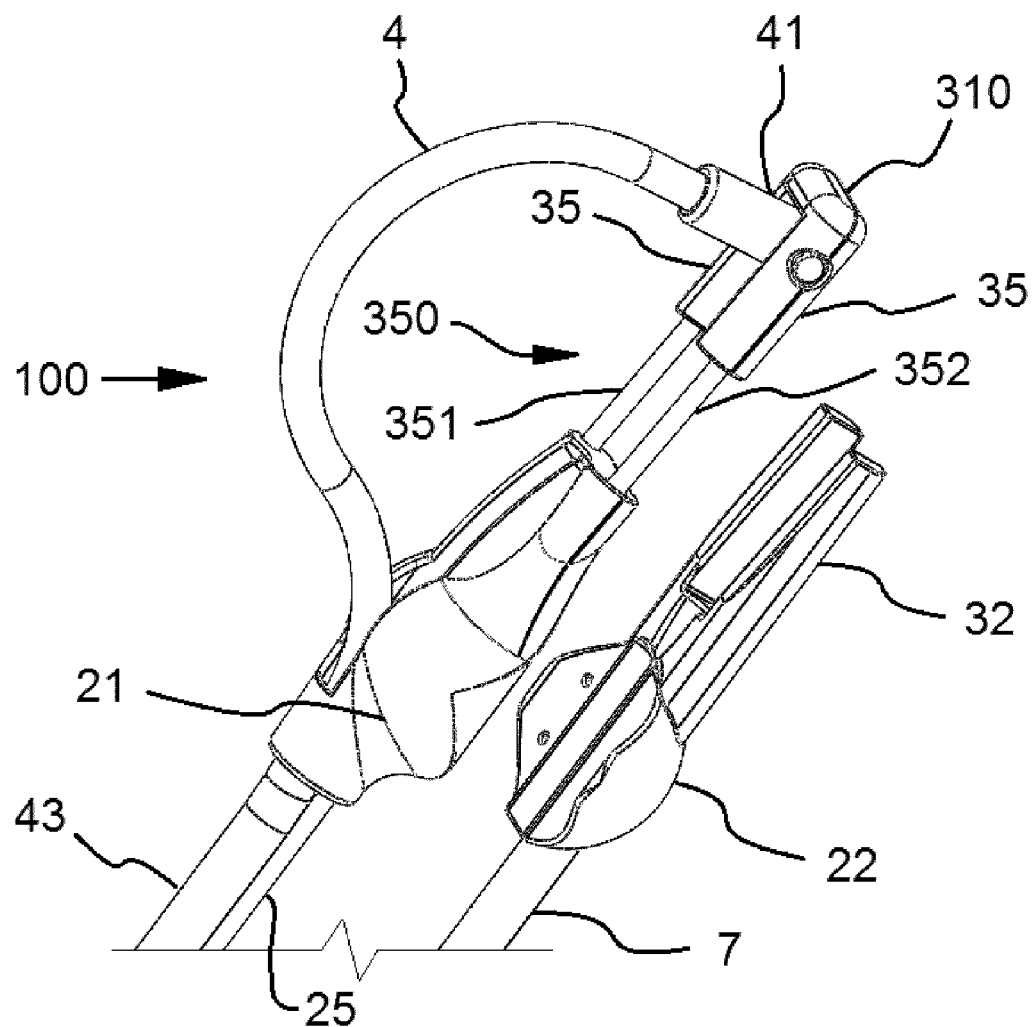
Figure 10:
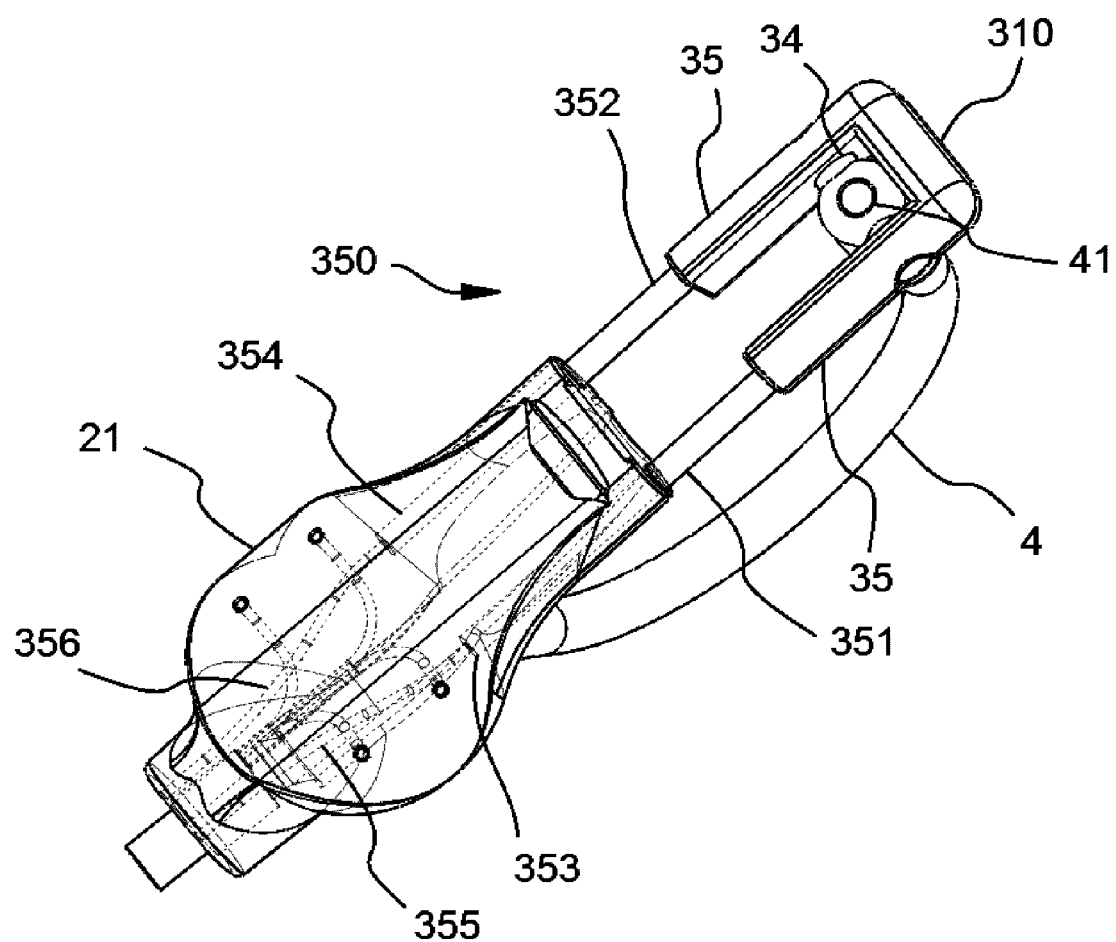
FIG. 10 represents a perspective view of the first clamping member and first projecting member of the device of FIGS. 8 and 9.
Figure 11:
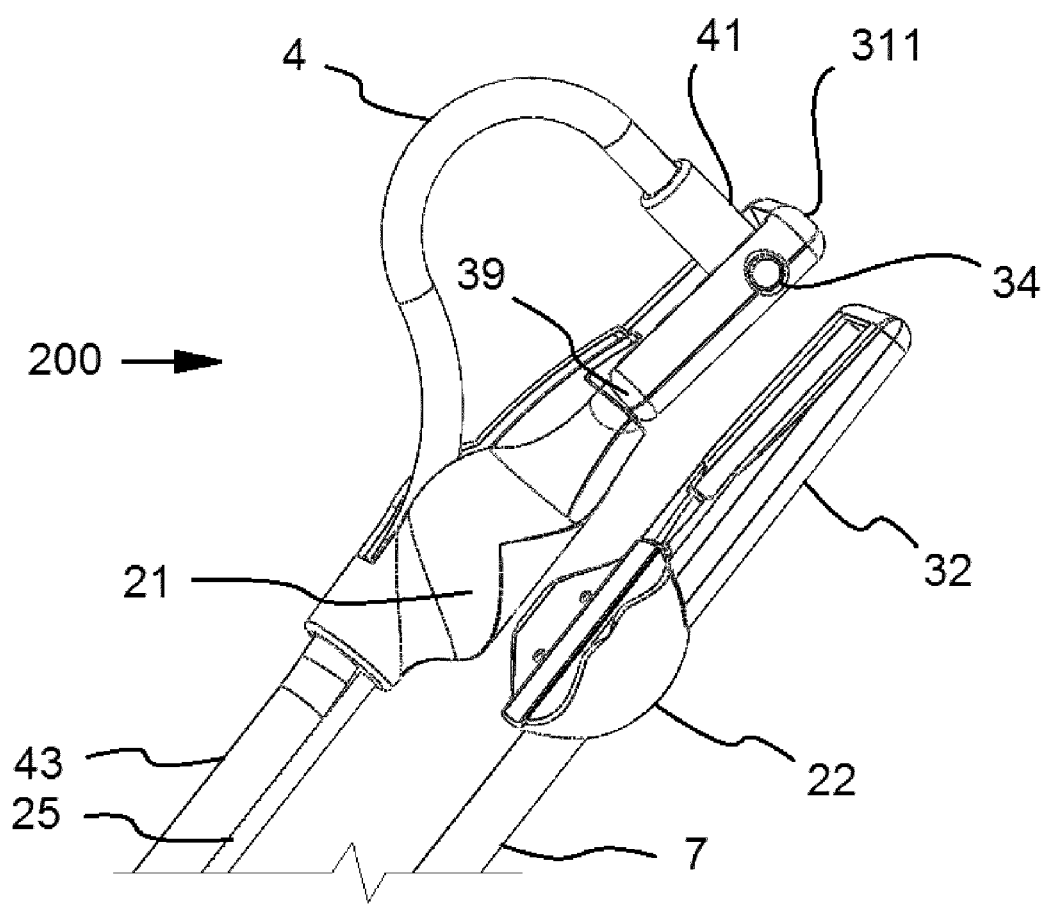
FIGS. 11 and 12 represent perspective views of the distal end of yet another embodiment of a device according to the invention.
Figure 12:
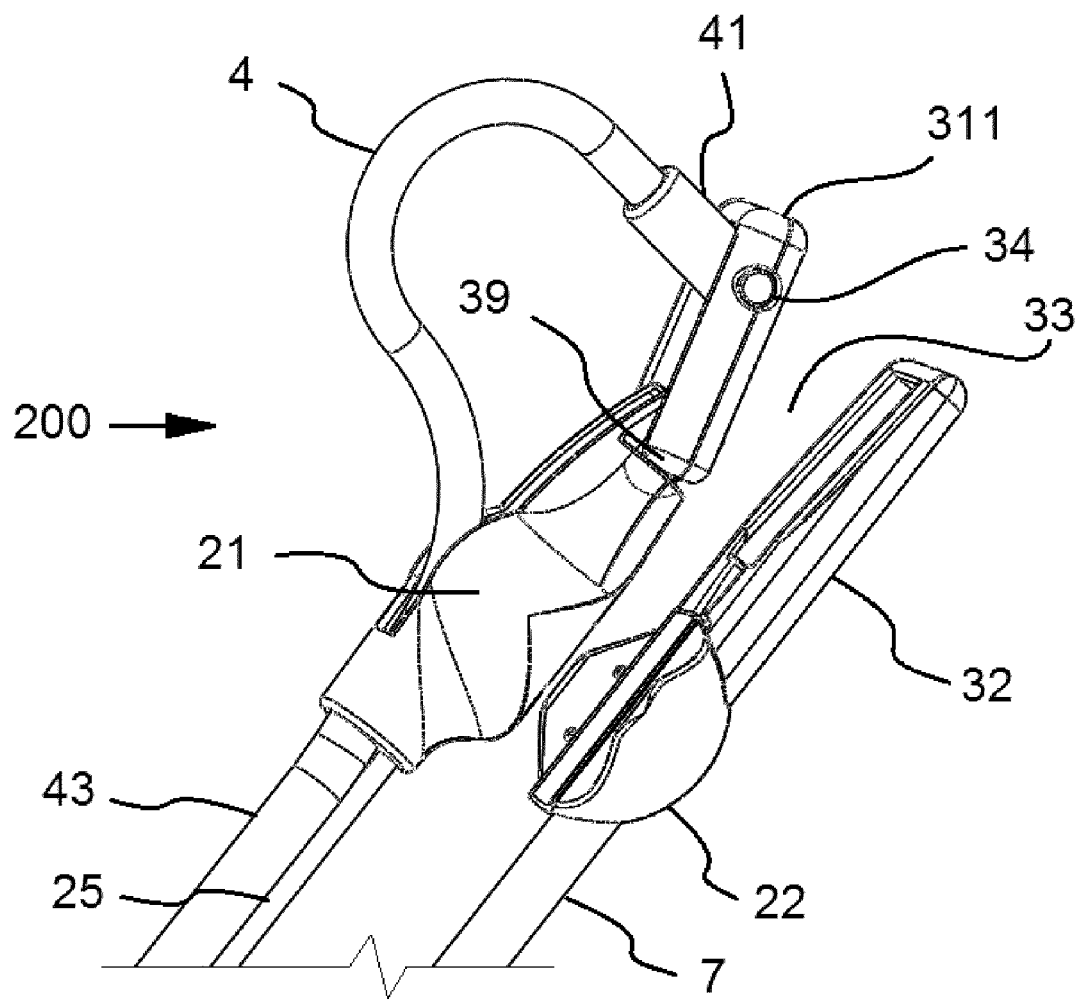
Figure 13:
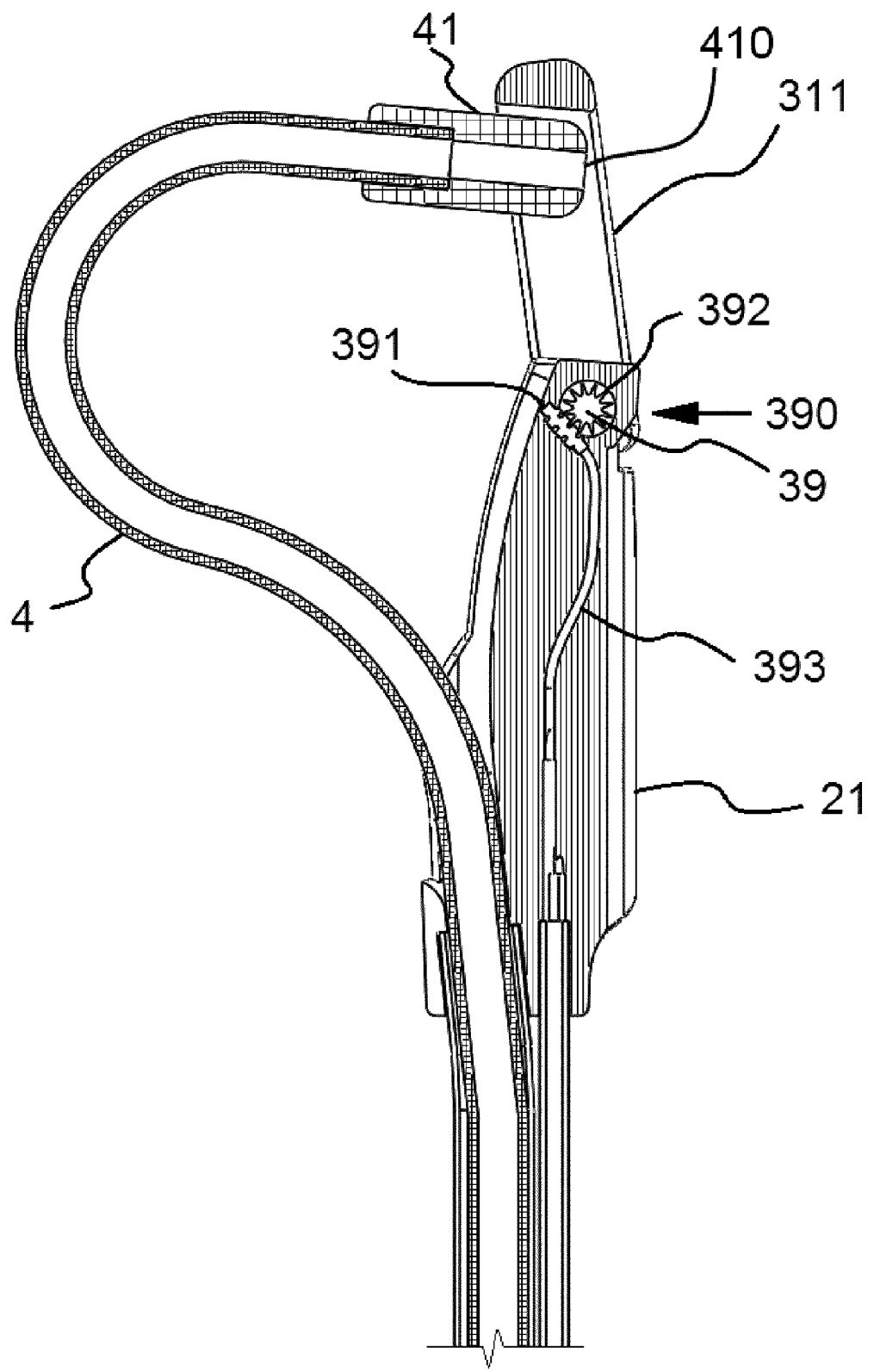
FIG. 13 represents a cross sectional view of the device of the first clamping and projecting members of FIG. 11.
Figure 14:
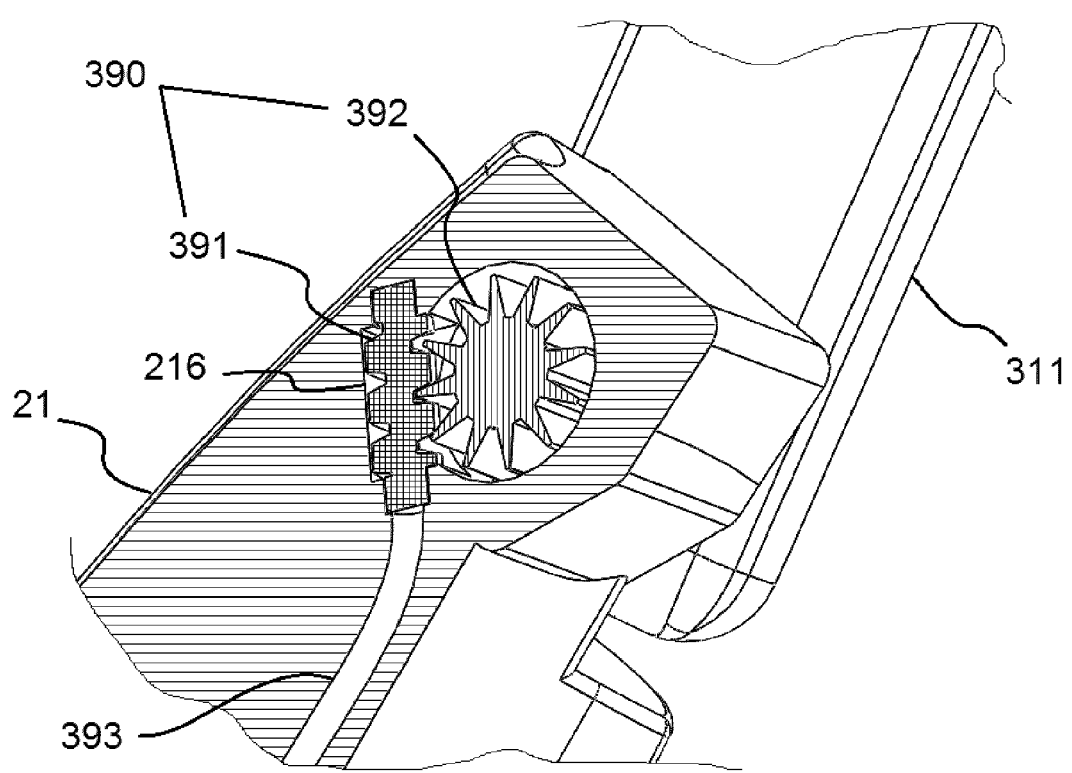
FIG. 14 represents a perspective view of a detail of the worm drive of FIG. 13.

FIGS. 8-10 show an embodiment of a device 100 according to the invention, which differs from device 1 of FIGS. 1-6 only in that the first bracket 310 is telescopically attached to the first clamping member 21. The first bracket 310 can hence be extended distally of the first clamping member 21 along a linear path. To this end, bracket 310 is mounted on a linear (telescopic) slide 350 (see FIG. 9, 10), which can be formed of two extension shafts 351, 352 configured to slide in corresponding seats 353, 354 arranged at a distal end of the clamping member 21. FIG. 8 shows the bracket 310 in a retracted position, whereas the bracket is shown in an extended position in FIG. 9. The extension shafts 351, 352 have distal ends fixedly secured to the legs 35 of the first bracket 31. They can be remotely actuated, such as by push wires (not shown) attached at proximal ends of the extension shafts and extending to a proximal end of the device 100. The push wires are accommodated in passages 355, 356 extending through the clamping member 21 and further in a cable duct (not shown) which guides them to the control handle of device 100.

The push wires can be locked in a desired position in a similar way as for the guide tube 4 or the attachment cables 23, 24 of device 10. Other ways of actuating and locking the extension shafts in position can be suitably used, as known in the art. As a result, the first bracket 31 can be fixed in a plurality of positions relative to the clamping member 21. In all such positions a rigid framework is obtained, due to the linear slide 350, allowing the guide tube 4 to be flexed and kept in position.

It will be convenient to note that the second bracket 32 can additionally or alternatively be similarly provided with a linear slide 350 as with bracket 310. Allowing one or both brackets to extend telescopically can be useful in gastric plication, since it allows to adjust the width of the tissue fold and hence control the distance between the suture point and the edge of the fold. It can also be useful for reducing bulkiness of the device during insertion in the patient by enabling to retract the bracket as much as possible towards the clamping member.

FIGS. 11-14 show another embodiment of a device 200 according to the invention, which differs from device 1 of FIGS. 1-6 only in that the first bracket 311, which is rigid, is pivotally attached to the first clamping member 21. The first bracket 311 can now be oriented relative to the first clamping member 21 according to a plurality of angular orientations. To this end, the first bracket 311 is attached to the first clamping member 21 through a pivot 39, which is more clearly shown in FIGS. 13-14. Pivot 39 can be formed of a shaft (not shown) which is fixed to the first bracket 311 and pivotally supported by the first clamping member 21. Pivot 39 advantageously extends parallel to the pivot axis 340 of pivot 34 which pivots the distal end 41 of guide tube 4. By pivoting bracket 311, a larger or smaller working space 33 can be created, since pivot 39 allows bracket 311 to be oriented such that its distal end points away from, or towards the second bracket 32.

Pivot 39 is advantageously remotely actuatable to change the angular orientation of the bracket 311 relative to the clamping member 21. To this end, a rotational actuator, such as a worm drive assembly 390 can be provided to actuate pivot 39. Worm drive 390 comprises a worm 391 meshing with a worm gear 392 which is coaxial with and fixed to the pivot 39. Worm 391 and worm gear 392 are rotatably housed in a recess 216 provided in the body of clamping member 21. Worm drive 390 is advantageously remotely actuatable. To this end, worm 391 is attached to the distal end of a wire 393 which extends to the proximal end of the device 200. Wire 393 can be turned in order to turn the worm 391, which in turn causes worm gear 392 and hence pivot 39 to rotate. As pivot 39 is fixed to the bracket 311, the orientation of the first bracket 311 can be changed remotely.

As with the linear slide 350, the actuator assembly 390 advantageously allows for fixing the first bracket 311 relative to the first clamping member 21 in at least one (angular) orientation, and preferably a plurality of orientations. In the example of FIGS. 11-14, it suffices to lock wire 393 in an angular position in order to lock the orientation of the bracket 311 relative to the clamping member 21. Needless to say, other ways of actuating the pivot 39 can be suitably implemented. What is important in this case, is that the bracket can be actuated to change orientation and that it can be fixed in at least one orientation relative to the clamping member, such that a rigid framework of clamping member and bracket is obtained as with the embodiment of FIGS. 1-6, which allows for supporting the guide tube 4 in the flexed position as shown in the FIGS. 11-13.

Advantageously, the pivotal arrangement of the first bracket 311 relative to the clamping member 21 enables the first bracket to be pivoted over a range of angles between −15°, advantageously −30°, advantageously −45°, and an angle of substantially 0°, advantageously +10°, advantageously +20°, advantageously +30°, wherein a negative angle refers to an orientation wherein the distal end of the first bracket points away from the second bracket 32, which corresponds to an increase of the working space 33, and a positive angle refers to an orientation wherein the distal end of the first bracket points towards the second bracket, which corresponds to a decrease of the working space 33. A zero angle corresponds to an orientation wherein the first bracket is parallel to the second bracket.

It will be convenient to note that, depending on the application, the orientation of pivot 39 need not be parallel to the pivot 34. Other orientations of pivot 39 are possible, which allow the first bracket to assume other orientations, e.g. pivotal motion sideways of the second bracket.

It will be convenient to note that in addition to the first bracket, or alternatively, the second bracket can be pivotally attached to the second clamping member in a similar fashion. Pivoting one or both brackets towards the working space can be useful in gastric plication operations in order to exert additional pressure on the tissue fold before starting to pierce through it. Pivoting one or both brackets away from the working space can be useful in same applications to ease release of the tissue from between the brackets.

It will also be convenient to note that the embodiments with respectively sliding arrangement and pivotal arrangement of the first bracket can be combined to obtain configurations wherein a distal end portion of the bracket, including the pivot 34 of the guide tube 4, can both be telescopically extended distally of and pivoted relative to the corresponding clamping member to obtain larger working spaces 33 and/or to minimize bulkiness of devices of the invention during endoluminal insertion in the patient.

Figure 15:
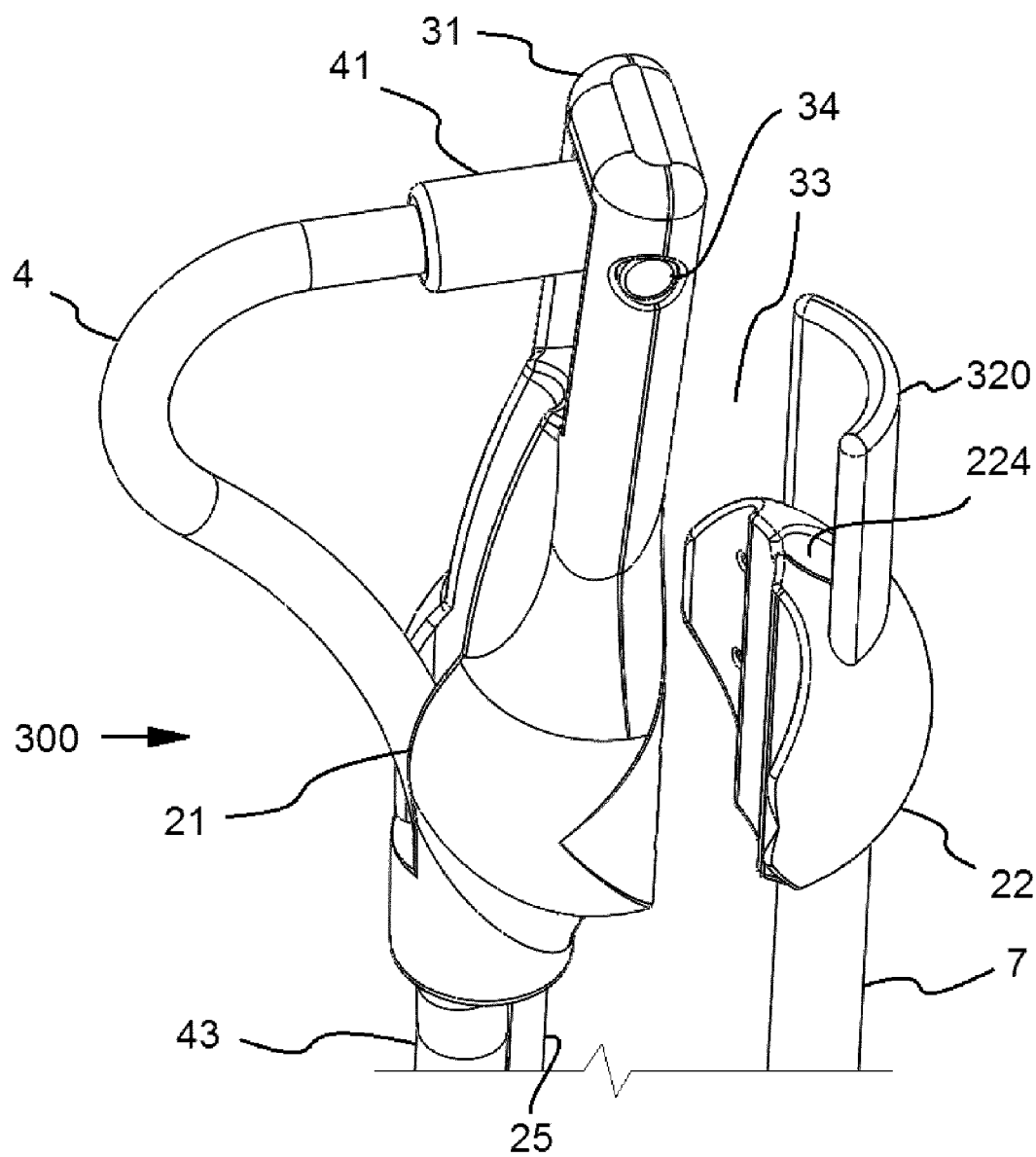
FIG. 15 represents a perspective view of the distal end of yet another embodiment of a device according to the invention.

FIG. 15 shows a device 300 according to the invention, which differs with regard to device 1 of FIGS. 1-6 only in the fact that the second projecting member is formed as a shielding wall 320.

Figure 16:
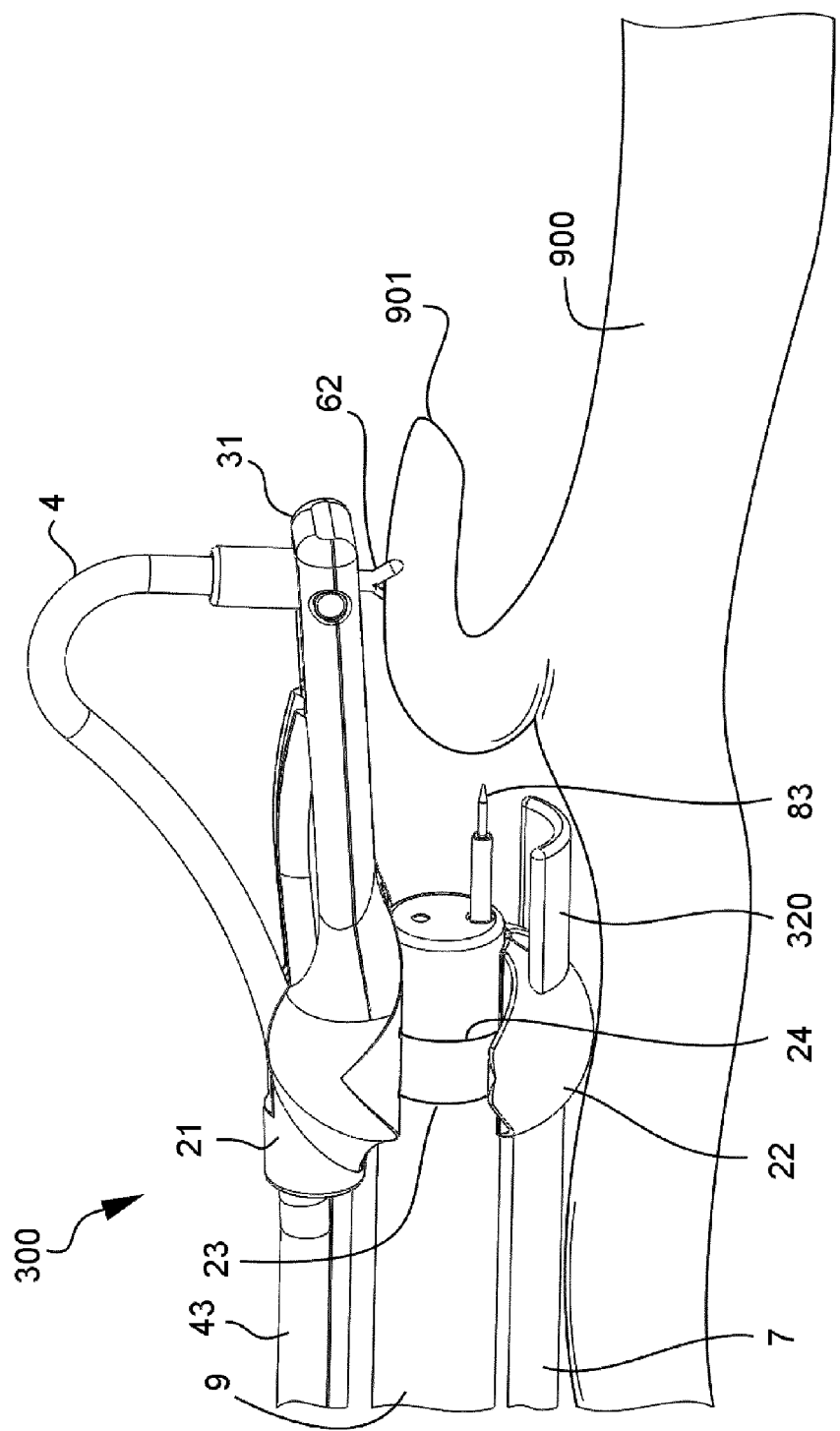
FIG. 16 represents schematically a mucosectomy procedure with the device of FIG. 15.

Device 300 is advantageously used in endoscopic mucosectomy interventions, as shown in FIG. 16. Most tumours of the digestive tract remain at the surface of the tissue (i.e. the mucosa) and therefore it is advantageous to remove only this small layer than having to perforate and remove a whole part of tissue. The removed tissue regenerates. To this end, a liquid solution is injected into the submucosa first. This one expands with the liquid solution, which causes the mucosa to lift, and enables to dissect the submucosa more easily. Two problems arise with this technique. Firstly, for medium to large tumours, there is easily a big flap of mucosa lying around during dissection. This hinders the vision of the endoscope very much. It is recommended to avoid piecemeal resection and keep the dissected flap of mucosa (with the tumour) in one piece in order to improve outcome of the operation. There is hence a need of a device which enables to lift the tissue so that it remains out of the field of the endoscope. Secondly, the layer below the submucosa—the muscular layer—must be protected from unwanted cutting. This is the more a problem for medium to large tumours, when a large flap of mucosa is being dissected, which hinders the vision of the endoscope and it becomes very difficult to see where the endoscopic tools are operating, such that there is a risk that the muscular layer gets cut, leading sometimes to undesired perforations of the tissue.

Devices of the invention can help in overcoming both problems. Referring to FIG. 16, the mucosa is dissected by means of an electric knife 83 which can be supported in the endoscope 9, or even in connecting tube 7 and throughpassage 224 of the second clamping member (see FIG. 15). Device 300 is provided with a first bracket 31 which is positioned relative to the clamping member 21 to assume a fixed position/orientation. Bracket 31 enables a grasper 62 supported inside guide tube 4 to lift a portion 901 of dissected mucosa out of the way. The lifting operation is greatly eased due to the fact that the (distal end of the) guide tube 4 can be flexed and locked in a whole range of orientations relative to the bracket 31, which is a clear advantage of devices according to the invention. A pivotal bracket and/or a telescopic bracket can improve handling.

The second projecting member 320, which is formed as a shielding wall, protects the muscular layer against undesired incisions and helps delineate the difference between the layers.

It is possible to use the connecting tube 7 and through passage 224 for accommodating a needle injecting the liquid solution to lift the mucosa. It is even possible to incorporate the knife 83 in the wall 320.

Figure 17:
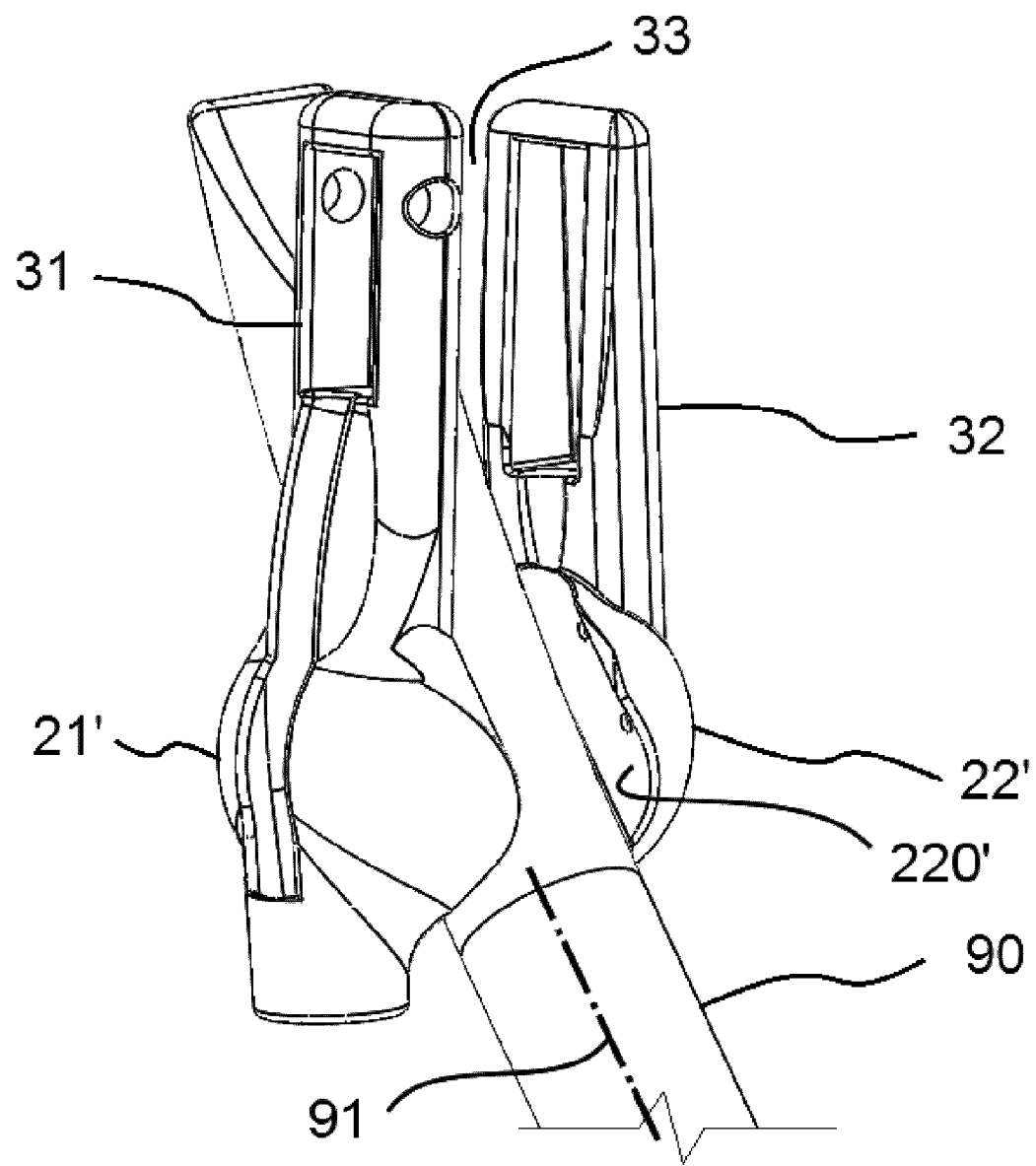
FIG. 17 represents a perspective view of the clamping members and projecting members of yet another embodiment of a device according to the invention for use with laterally viewing endoscopes.

Devices according to the invention can advantageously be used with endoscopes with lateral view as shown in FIG. 17.

It suffices to modify the inner surfaces 220' of the clamping members 21', 22' in order to accommodate the endoscope 90 obliquely relative to the projecting members 31 and 32. Inner surfaces 220' are aligned with axis 91 of endoscope 90, which is oblique to the direction of extension of projecting members 31, 32. By so doing, a working space 33 is created sideways of the endoscope 90, which can be viewed at laterally by the scope. In FIG. 17, the connecting tubes, as well as the guide tube and the pivot of the guide tube are not represented for reasons of clarity.

It will be convenient to note that the projecting members can be provided with more degrees of freedom, as long as they can be fixed in at least one position or orientation in order to obtain a rigid framework.

It can be suitable for some applications, to make the second projecting member symmetrically identical to the first projecting member, i.e. to provide a second endoscopic tool guide tube 4 and to attach a distal end of it pivotally to a distal end of the second bracket, such that the guide tube can assume a flexed position with its distal end oriented transversely to the bracket.

Besides applications of transoral gastric plication and mucosectomy, devices of the invention can advantageously be used for fistula closure.

It clearly follows from the above description that devices according to the invention are of a simple construction, yet allow for obtaining unrivalled results.

The invention claimed is:

1. A device for supporting an endoscopic tool, comprising:
   an attachment apparatus for attaching the device to an endoscope;
   a first guide tube configured for accepting the endoscopic tool, the first guide tube having a distal end, the distal end having a distal opening; and
   a first and a second projecting members extending distally of the attachment apparatus and which are spaced apart when the device is attached to the endoscope to define a working space between the first and second projecting members,
   wherein the attachment apparatus comprises a first and a second clamping members and at least one cable linking the clamping members, wherein the cable is remotely actuatable and configured to move the clamping members relative to each other by adjusting a spacing between the clamping members, and wherein locking the cable holds the clamping members in a clamping position during insertion of the endoscope in the spacing between the clamping members and to secure the clamping members to the endoscope;
   the first projecting member is attached to the first clamping member and configured with at least one fixable position relative to the first clamping member, and the second projecting member is attached to the second clamping member;
   the first guide tube is slidable relative to the first clamping member, and the distal end of the first guide tube is pivotally attached to a distal end of the first projecting member and configured to pivot the distal end of the first guide tube to an orientation transverse to the first projecting member; and
   the distal end of the first guide tube is in communication with the working space when in the transverse orientation.

2. The device of claim 1, wherein one or more of the first projecting member or the second projecting member is a rigid member.

3. The device of claim 1, wherein the second projecting member is attached to the second clamping member and configured with at least one fixable position relative to the second clamping member.

4. The device of claim 1, wherein the first projecting member comprises opposite spaced apart uprights and a pivoting axis extending between the uprights, wherein the distal end of the first guide tube is secured to the pivoting axis between the uprights.

5. The device of claim 1, wherein the second projecting member comprises a through opening at a position opposite the distal end of the first guide tube, wherein the through opening is in facing relationship with the distal end and configured to allow the endoscopic tool to move past the second projecting member and through the through opening.

6. The device of claim 1, wherein the first projecting member comprises a stop member to which the distal end of the first guide tube abuts when in the transverse orientation configuration.

7. The device of claim 6, wherein the stop member comprises an aperture configured to maintain the distal opening of the distal end of the first guide tube clear when the first guide tube is in a substantially parallel orientation to the first projecting member.

8. The device of claim 1, wherein the first projecting member comprises a cap member disposed distally of the distal end of the first guide tube configured to close the first guide tube when in a substantially parallel orientation to the first projecting member.

9. The device of claim 1, comprising an apparatus configured to lock the first guide tube in a plurality of orientations relative to the first projecting member.

10. The device of claim 1, wherein the first guide tube is pivotally attached to the distal end of the first projecting member and configured to pivot the distal end of the first guide tube to an orientation substantially perpendicular to the first projecting member.

11. The device of claim 1, wherein the clamping members are shaped to have a length of engagement with the endoscope smaller than or equal to 50 mm-measured axially along the endoscope.

12. The device of claim 1, wherein one or more of the second clamping member or the second projecting member comprise a through passage proximally connected to a second guide tube and distally in communication with the working space, for accepting a second endoscopic tool.

13. The device of claim 1, wherein the first projecting member is telescopically attached to the first clamping member through linear sliding means, the first projecting member is configured to extend distally of the first clamping member to increase a distance between the first clamping member and the pivotal attachment of the first guide tube to the first projecting member, and wherein the device is configured to fix the linear sliding means in a plurality of positions of the first projecting member relative to the first clamping member.

14. The device of claim 1, wherein the first projecting member is pivotally attached to the first clamping member, the device is configured to fix the first projecting member in a plurality of angular orientations relative to the first clamping member.

15. The device of claim 1, wherein the first projecting member is secured to the first clamping member in a fixed position relative to the first clamping member.

16. The device of claim 15, wherein the first projecting member is made integral with the first clamping member.

17. The device of claim 1, wherein the second projecting member is secured to the second clamping member in a fixed position relative to the latter.

18. The device of claim 17, wherein the second projecting member is made integral with the second clamping member.

19. The device of claim 1, wherein the first and second clamping members comprise internal surfaces configured to engage the endoscope in the clamping position, the internal surfaces having an axis which is oblique to the direction of distal extension of the first and second projecting members.

20. The device of claim 1, wherein remote actuation of the cable provides for moving the clamping members relative to each other to adjust a spacing between the clamping members such that the clamping members can be held in one or more of:
  (i) a closed position corresponding to a configuration wherein the spacing is minimal and the clamping members provide minimal bulkiness,
  (ii) an open position wherein the spacing is such that the endoscope can be inserted through the spacing, and
  (iii) a clamping position wherein the spacing is such that the endoscope is clamped between the clamping members.

* * * * *